United States Patent [19]

Nickl et al.

[11] Patent Number: 4,929,754

[45] Date of Patent: May 29, 1990

[54] BENZENESULPHONAMIDOINDANYL COMPOUNDS

[75] Inventors: Josef Nickl; Armin Heckel; Erich Muller; Berthold Narr; Johannes Weisenberger; Wolfgang Eisert; Thomas Muller, all of Biberach, Fed. Rep. of Germany

[73] Assignee: Dr. Karl Thomae GmbH, Biberach an der Riss, Fed. Rep. of Germany

[21] Appl. No.: 305,255

[22] Filed: Feb. 1, 1989

Related U.S. Application Data

[62] Division of Ser. No. 73,950, Jul. 16, 1987, Pat. No. 4,820,705.

[30] Foreign Application Priority Data

Jul. 16, 1986 [DE] Fed. Rep. of Germany ....... 3623944

[51] Int. Cl.$^5$ .......................................... C07C 147/107

[52] U.S. Cl. ..................................... 562/428; 560/10; 560/16

[58] Field of Search .................... 562/428; 560/10, 16

[56] References Cited

U.S. PATENT DOCUMENTS 4,233,457 11/1980 Czaja et al. ......................... 562/428
4,748,271 5/1988 Meneghin ............................ 562/428

Primary Examiner—Werren B. Lone
Assistant Examiner—Vera C. Clarke
Attorney, Agent, or Firm—D. E. Frankhouser; M-E. M. Timbers; A. R. Stempel

[57] ABSTRACT

The invention relates to new benzenesulphonamidoindanyl compounds useful in the treatment and prophylaxis of thromboembolic diseases, arteriosclerosis and tumor metastasis.

7 Claims, No Drawings

BENZENESULPHONAMIDOINDANYL COMPOUNDS

This is a division of application Ser. No. 073,950, filed Jul. 16, 1987, now U.S. Pat. No. 4,820,705.

The present invention relates to new benzenesulphonamidoindanyl compounds of the general formula

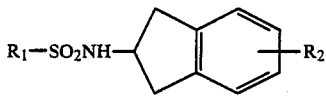 (I)

to enantiomers thereof and addition salts thereof, particularly physiologically acceptable addition salts thereof with inorganic or organic bases for pharmaceutical use, where $R_2$ represents or contains a hydroxycarbonyl group, which compounds possess valuable pharmacological properties, in particular an antithrombotic action; in addition the new compounds are thromboxane antagonists.

The present invention therefore relates to the new compounds of the general formula I above, to addition salts thereof with inorganic or organic bases, particularly physiologically acceptable addition salts thereof for pharmaceutical use, to medicaments containing these compounds and to processes for their preparation.

In the above general formula $R_1$ denotes a phenyl group which is optionally monosubstituted or disubstituted by a halogen atom or a methyl or methoxy group, it being possible for the substituents to be identical or different, and $R_2$ denotes a hydroxycarbonyl group or alkoxycarbonyl group which has a total of 2 to 4 carbon atoms which groups are optionally attached via an alkylene group having 1 to 5 carbon atoms or via an alkenylene group having 2 to 5 carbon atoms, it being possible in each case for a methylene group in the above-mentioned alkylene or alkenylene radicals, which methylene group must be attached to the indanyl radical, to be replaced by a hydroxymethylene or carbonyl group, and, at the same time, for the methylene group via which the above-mentioned alkoxycarbonyl group is attached to be substituted by a further alkoxycarbonyl group having a total of 2 to 4 carbon atoms, or $R_2$ denotes a 4,5-dihydro-pyridazin-3(2H)-on-6-yl or pyridazin-3(2H)-on-6-yl group which can be substituted in the 4position or 5-position by an alkyl group having 1 to 3 carbon atoms and/or in the 4-position by an alkoxycarbonyl group having a total of 2 to 4 carbon atoms.

The following are possible examples of the meanings mentioned initially in defining the radicals $R_1$ and $R_2$: in the case of $R_1$ the phenyl, 2-methylphenyl, 3-methylphenyl, 4-methylphenyl, 2-methoxyphenyl, 3-methoxyphenyl, 4-methoxyphenyl, 2-fluorophenyl, 3-fluorophenyl, 4-fluorophenyl, 2-chlorophenyl, 3-fluorophenyl, 4-fluorophenyl, 2-chlorophenyl, 3-chlorophenyl, 4-chlorophenyl, 2-bromophenyl, 4-bromophenyl, 3,4-dimethylphenyl, 3,4-dimethoxyphenyl, 2,4-difluorophenyl, 2,4-dichlorophenyl, 2,5-dichlorophenyl, 2,4-dibromophenyl or methylchlorophenyl group and, in the case of $R_2$, the hydroxycarbonyl, hydroxycarbonylmethyl, 1-hydroxycarbonyl-ethyl, 2-hydroxycarbonyl-ethyl, 1-hydroxycarbonyl-propyl, 3-hydroxycarbonyl-propyl, 1-hydroxycarbonyl-butyl, 4-hydroxycarbonyl-butyl, 1-hydroxycarbonyl-1-methyl-ethyl, 2-hydroxycarbonyl-1-methyl-ethyl, 2-hydroxycarbonylethenyl, 2-hydroxycarbonyl-1-methyl-ethenyl, 3-hydroxycarbonyl-propenyl, 2-hydroxycarbonylethanon-1-yl, 3-hydroxycarbonyl-n-propanon-1-yl, 4-hydroxy- carbonyl-n-butanon-1-y), 5-hydroxycarbonyl-n-pentanon-1-yl, 2-hydroxycarbonyl-2-methyl-ethanon-1-yl, 3-hydroxycarbonyl-2-methyl-n-propanon-1-yl, 3-hydroxycarbonyl-3-methyl-n-propanon-1-yl, 4-hydroxycarbonyl-2-methyl-n-butanon-1-yl, 4-hydroxycarbonyl-3-methyl-n-butanon-1-yl, 4-hydroxycarbonyl-4-methyl-n-butanon-1-yl, 2-hydroxycarbonyl-2-ethylethanon-1-yl, 2-hydroxycarbonyl-2-n-propyl-ethanon-1-yl, 2-hydroxycarbonyl-2-ethyl-n-propanon-1-yl, 3-hydroxycarbonyl-3-ethyl-n-propanon-1-yl, 4-hydroxycarbonyl-n-butene-2-on-1-yl, 5-hydroxycarbonyl-n-penten-2-on-1-yl, 2-hydroxycarbonyl-1-hydroxy-ethyl, 3-hydroxy-carbonyl-1-hydroxy-n-propyl, 4-hydroxycarbonyl-1-hydroxy-n-butyl, 5-hydroxycarbonyl-1-hydroxy-n-pentyl, 2-hydroxycarbonyl-2-methyl-1-hydroxy-ethyl, 2-hydroxycarbonyl-2-ethyl-1-hydroxyethyl, 2-hydroxycarbonyl-2-isopropyl-1-hydroxy-ethyl, 3-hydroxycarbonyl-2-methyl-1-hydroxy-n-propyl, 3-hydroxycarbonyl-2-ethyl-1-hydroxy-n-propyl, 3-hydroxycarbonyl-3-methyl-1-hydroxy-n-propyl, 3-hydroxycarbonyl-3-ethyl-1-hydroxy-n-propyl, 4-hydroxycarbonyl-2-methyl-1-hydroxy-n-butyl, 4-hydroxycarbonyl-3-methyl-1-hydroxy-n-butyl, 4-hydroxycarbonyl-4-methyl-1-hydroxy-n-butyl, methoxycarbonyl, ethoxycarbonyl, n-propoxycarbonyl, methoxycarbonylmethyl, ethoxycarbonylmethyl, isopropoxycarbonylmethyl, 2-methoxycarbonyl-ethyl, 2-ethoxycarbonyl-ethyl, 3-methoxycarbonyl-propyl, 4-ethoxycarbonylbutyl, 2-methoxycarbonyl-1-methylethyl, 2-ethoxycarbonyl-1-methyl-ethyl, 2-isopropoxycarbonyl-1-methyl-ethyl, 2-methoxycarbonyl-ethenyl, 2-methoxycarbonyl-1-methylethenyl, 2-ethoxycarbonyl-1 -methyl-ethenyl, 3-methoxycarbonylpropenyl, 2-methoxycarbonyl-ethanon-1-yl, 2-(2-methoxyethoxycarbonyl)-ethanon-1-yl, 3-methoxycarbonyl-n-propanon-1-yl, 3-ethoxycarbonyl-n-propanon-1-yl, 3-(2-ethoxy-ethoxy- carbonyl)-n-propanon-1-yl, 3-(3-methoxy-n-propoxy-carbonyl)-n-propanon-1-yl, 3-n-propoxycarbonyl-n-propanon-1-yl, 4-ethoxycarbonyl-n-butanon-1-yl, 5-ethoxycarbonyl-n-pentanon-1-yl, 2-ethoxycarbonyl-2-methylethanon-1-yl, 3-ethoxycarbonyl-2-methyl-n-propanon-1-yl, 3-ethoxycarbonyl-3-methyl-n-propanon -1-yl, 4-ethoxycarbonyl-2-methyl-n-butanon-1-yl, 4-ethoxycarbonyl-3-methyl-n-butanon-1-yl, 4-ethoxycarbonyl-4-methyl-n-butanon-1-yl, 2-ethoxycarbonyl-2-ethyl-ethanon-1-yl, 2-ethoxycarbonyl-2-n-propyl-ethanon-1-yl, 3-ethoxycarbonyl-2-ethyl-n-propanon-1-yl, 3-ethoxycarbonyl-3-ethyl-n-propanon-1-yl, 3-ethoxycarbonyl-n-propanon-1-yl, 3-ethoxycarbonyl-2-methyl-n-propanon-1-yl, 3-ethoxycarbonyl-3-methyl-n-propanon-1-yl, 4-ethoxycarbonyl-n-buten-2-on-1-yl, 5-ethoxycarbonyl-n-penten-2-on-1-yl, ethoxycarbonyl-hydroxymethyl, 2-ethoxycarbonyl-1-hydroxyethyl, 3-ethoxycarbonyl-1-hydroxy-n-propyl, 4-ethoxycarbonyl-1-hydroxy-n-butyl, 5-ethoxycarbonyl-1-hydroxy-n-pentyl, 2-ethoxycarbonyl-2-methyl-1-hydroxy-ethyl, 2-ethoxycarbonyl-2-ethyl-1-hydroxy-ethyl, 2-ethoxy- carbonyl-2-isopropyl-1-hydroxy-ethyl, 3-ethoxycarbonyl-2-methyl-1-hydroxy-n-propyl, 3-ethoxycarbonyl-2-ethyl-1-hydroxy-n-propyl, 3-ethoxycarbonyl-3-methyl-1-hydroxy-n-propyl, 3-ethoxycarbonyl-3-ethyl-1-hydroxy-n-propyl, 4-ethoxycarbonyl-2-methyl-1-hydroxy-n-butyl, 4-ethoxycarbonyl-3-methyl-1- hydroxy-n-butyl, 4-ethoxycarbonyl-4-methyl-1-hydroxy-n-butyl, 4,5-dihydro-pyridazin-3(2H)-on-6-yl, 4,5-dihydro- 5-methyl-pyridazin-3(2H)-on-6-yl, 4,5-dihydro-5-ethyl-pyridazin-3(2H)-on-6-yl, 4,5-dihydro-5-n-propyl-pyridazin-3(2H)-on-6-yl, pyridazin-3(2H)-on-6-yl, 5-methyl-pyridazin-3(2H)-on-6-yl, 5-ethylpyridazin-3(2H)-on-6-yl, 5-n-propyl-pyridazin-3(2H)-on-6-yl, 5-isopropyl-pyridazin-3(2H)-on-6-yl, 5-isopropyl-pyridazin-3(2H)-on-6-yl, 4,5-dihydro-4-methoxycarbonyl-pyridazin-3(2H)-on-6-yl, 4,5-dihydro-4-ethoxycarbonyl-pyridazin-3(2H)-on-6-yl, 4,5-dihydro-4-n-propoxycarbonyl-pyridazin-3(2H)-on-6-yl, 4,5-dihydro-4-isopropoxycarbonyl-pyridazin-3(2H)-on-6-yl, 4,5-dihydro-4-methoxycarbonyl-5-methylpyridazin-3(2H)-on-6-yl, 4,5-dihydro-4-ethoxycarbonyl-5-methyl-pyridazin-3(2H)-on-6-yl, 4,5-dihydro-4-n-propoxycarbonyl-5-methyl-pyridazin-3(2H)-on -6-yl, 4,5-dihydro-4-ethoxycarbonyl-5-ethylpyridazin-3(2H)-on-6-yl, 4,5-dihydro-4-ethoxycarbonyl-5-n-propyl-pyridazin-3(2H)-on-6-yl, 4-ethoxycarbonyl-pyridazin-3(2H)-on-6-yl, 5-methyl-4-ethoxycarbonyl-pyridazin-3(2H)-on-6-yl, 5-ethyl-4 -ethoxycarbonyl-pyridazin-3(2H)-on-6-yl, 5-n-propyl-4-ethoxycarbonyl-pyridazin-3(2H)-on-6-yl or 5-isopropyl-4-ethoxycarbonyl-pyridazin-3(2H)-on-6-yl group.

Preferred compounds of the above general formula I are those in which $R_1$ denotes a phenyl group which is optionally substituted by a methyl or methoxy group or denotes a phenyl group which is monosubstituted or disubstituted by a fluorine, chlorine or bromine atom, and $R_2$ denotes a hydroxycarbonyl group or alkoxycarbonyl group which has a total of 2 or 3 carbon atoms which groups are optionally attached via a linear or branched alkylene group having 1 to 4 carbon atoms or via a linear or branched alkenylene group having 2 to 4 carbon atoms, it being possible in each case for a methylene group in the above-mentioned alkylene or alkenylene groups, which methylene group must be attached to the indanyl radical, to be replaced by a hydroxymethylene or carbonyl group, or denotes a 4,5-dihydropyridazin-3(2H)-on-6-yl or pyridazin-3(2H)-on-6-yl group which is optionally substituted in the 5-position by a methyl group and which can additionally be substituted in the 4-position by an alkoxycarbonyl group having a total of 2 or 3 carbon atoms.

Compounds of the above general formula I which are particularly preferred are, however, those in which $R_1$ denotes phenyl group which is optionally substituted by a fluorine or chlorine atoms or by a methyl or methoxy group, and $R_2$ denotes a hydroxycarbonylmethyl, 4-hydroxycarbonyl-n-propyl, 3-hydroxycarbonyl-n-propanon-1-yl, 4,5-dihydro-pyridazin-3(2H)-on-6-yl or 4,5-dihydro-5-methyl-pyridazin-3(2H)-on-yl group.

The new compounds are obtained in accordance with the invention by the following processes:

(a) acylating a compound of the general formula

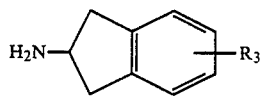
(II)

in which $R_3$ has the meanings mentioned initially for $R_2$, but in which a hydroxyl group in the radical $R_2$ can be protected by a protecting group capable of being split off by hydrolysis or hydrogenolysis, such as an alkoxy or benzyloxy group, with a phenyl- sulphonic acid derivative of the general formula $$R_1 - SO_2X \qquad (III)$$

in which $R_1$ is as defined initially and

X represents a nucleophilic leaving group, such as a halogen atom or an alkoxy group, for example a chlorine or bromine atom or a methoxy or ethoxy group, and, if appropriate, subsequently splitting off a protecting radical which has been used.

The reaction is preferably carried out in a solvent, such as methanol, ethanol, water/methanol, dioxan, tetrahydrofuran or chloroform, and if appropriate in the presence of an acid-binding agent, such as potassium carbonate, triethylamine or pyridine, it being possible for the two last agents also to be used as the solvent, suitably at temperatures between 0° and 50° C., but preferably at room temperature.

The optional subsequent elimination of a protective radical used is preferably effected by hydrolysis in an aqueous solvent, for example in water, isopropanol/water, tetrahydrofuran/water or dioxan/water, in the presence of an acid, such as hydrochloric acid or sulphuric acid, or in the presence of an alkali metal base, such as sodium hydroxide or potassium hydroxide, and at temperatures between 0° and 100° C., preferably at the boiling point of the reaction mixture. The elimination of a benzyl radical is, however, preferably effected by hydrogenolysis, for example by means of hydrogen in the presence of a catalyst, such as palladium/charcoal, in a solvent, such as methanol, ethanol, ethyl acetate or glacial acetic acid, if appropriate with the addition of an acid, such as hydrochloric acid, at temperatures between 0° and 50° C., but preferably at room temperature, and under a hydrogen pressure of 1 to 7 bar, but preferably 3 to 5 bar.

(b) For the preparation of compounds of general formula I in which $R_2$ represents or contains a hydroxycarbonyl group:

Eliminating a protecting radical from a compound of the general formula

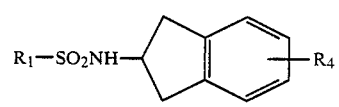
(IV)

in which $R_1$ is as defined initially and $R_4$ has the meanings mentioned initially for $R_2$, but in which the carboxyl group is protected by a protecting group capable of being split off by hydrolysis, thermolysis or hydrogenolysis, or $R_4$ represents a functional derivative of the carboxyl group and/or the radical $R_2$ contains a hydroxyl group which is protected by a protecting radical.

Examples of possible hydrolysable groups are functional derivatives of the carboxyl group, such as unsubstituted or substituted amides, esters, thioesters, orthoesters, iminoethers, amidines or anhydrides thereof, the nitrile group, ether groups, such as the methoxy or benzyloxy group, or lactones, and examples of possible groups which can be split off by thermolysis are esters with tertiary alcohols, for example the tert.-butyl ester, and examples of possible groups capable of being split off by hydrogenolysis are aralkyl groups, for example the benzyl group.

The hydrolysis is suitably carried out either in the presence of an acid, such as hydrochloric acid, sulphuric acid, phosphoric acid or trichloroacetic acid, or in the presence of a base, such as sodium hydroxide or potassium hydroxide, in a suitable solvent, such as water, water/methanol, ethanol, water/ethanol, water/isopropanol or water/dioxan, at temperatures between −10° and 120° C., for example at temperatures between room temperature and the boiling point of the reaction mixture.

If, for example, a compound of the general formula IV contains a nitrile or aminocarbonyl group, these groups can be converted into the carboxyl group, preferably by means of 100% strength phosphoric acid at temperatures between 100° and 180° C., preferably at temperatures between 120° and 160° C., or by means of a nitrite, for example sodium nitrite, in the presence of an acid, such as sulphuric acid, the latter being suitably used at the same time as the solvent, at temperatures between 0° and 50° C.

If, for example, a compound of the general formula IV contains the tert.-butoxycarbonyl group, the tert.-butyl group can also be split off thermally, if appropriate in an inert solvent, such as methylene chloride, chloroform, benzene, toluene, tetrahydrofuran or dioxan, and preferably in the presence of a catalytic amount of an acid, such as p-toluenesulphonic acid, sulphuric acid, phosphoric acid or polyphosphoric acid, preferably at the boiling point of the solvent used, for example at temperatures between 40° and 100° C.

If, for example, a compound of the general formula IV contains the benzyloxy or benzyloxycarbonyl group, the benzyl group can also be split off by hydrogenolysis in the presence of a hydrogenation catalyst, such as palladium/charcoal, in a suitable solvent, such as methanol, ethanol, methanol/water, ethanol/water, glacial acetic acid, ethyl acetate, dioxan or dimethylformamide, preferably at temperatures between 0° and 50° C., for example at room temperature, and under a hydrogen pressure of 1 to 5 bar. In the course of the hydrogenolysis it is possible at the same time to dehalogenate a halogen-containing compound and to hydrogenate a double bond present.

(c) For the preparation of compounds of the general formula I in which $R_2$ contains, adjacent to the indanyl radical, a carbonyl group:
Acylating a compound of the general formula

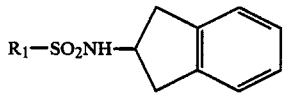 (V)

in which
  $R_1$ is as defined initially, by means of a compound of the general formula Y - $R_5$ (VI)
in which
  $R_5$ has the meanings mentioned initially for $R_2$, but in which $R_2$ must contain, adjacent to Y, a carbonyl group and in which, at the same time, a hydroxycarbonyl group which may be present can be protected by means of a protecting radical capable of being split off by hydrolysis or hydrogenolysis, such as an alkoxy or benzyl group, and
  Y represents a nucleophilic leaving group, such as a halogen atom, for example a chlorine, bromine or iodine atom, or the anhydride thereof, in the presence of a Lewis acid and, if appropriate, subsequently eliminating a protecting radical used.

The Friedel-Crafts acylation is preferably carried out in a solvent, such as ethylene chloride or nitrobenzene, in the presence of a Lewis acid, such as aluminium chloride, boron trifluoride or zinc chloride, suitably at temperatures between 0° and 50° C., but preferably at room temperature.

The optional subsequent elimination of a protecting radical used is preferably effected by hydrolysis in an aqueous solvent, for example in water, isopropanol/water, tetrahydrofuran/water or dioxan/water, in the presence of an acid, such as hydrochloric acid or sulphuric acid, or in the presence of an alkali metal base, such as sodium hydroxide or potassium hydroxide, at temperatures between 0° and 100° C., preferably at the boiling point of the reaction mixture. The elimination of a benzyl radical is, however, preferably effected by means of hydrogenolysis, for example by means of hydrogen in the presence of a catalyst, such as palladium/charcoal, in a solvent, such as methanol, ethanol, ethyl acetate or glacial acetic acid, if appropriate with the addition of an acid, such as hydrochloric acid, at temperatures between 0 and 50° C., but preferably at room temperature, and under a hydrogen pressure of 1 to 7 bar, but preferably 3 to 5 bar.

(d) For the preparation of compounds of the general formula I in which $R_2$ contains, adjacent to the indanyl radical, a hydroxymethylene or methylene group:
Reducing a compound of the general formula

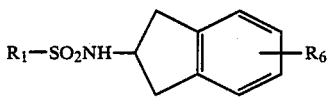 (VII)

in which
  $R_1$ is as defined initially and
  $R_6$ has the meanings mentioned initially for $R_2$, but in which $R_2$ must contain, adjacent to the indanyl radical, a carbonyl group.

The reduction is carried out in a suitable solvent, such as methanol, ethanol, ether, tetrahydrofuran, dioxan or glacial acetic acid, in the presence of catalytically activated hydrogen, for example hydrogen in the presence of platinum or palladium/charcoal, and, if appropriate, in the presence of an acid, such as hydrochloric acid or perchloric acid or in the presence of a metal hydride, such as sodium borohydride, lithium borohydride or lithium aluminium hydride, at temperatures between 0° and 100° C., preferably at temperatures between 20° and 80° C.

For the preparation of a compound of the general formula I in which $R_2$ contains a hydroxymethylene group, the reaction is preferably carried out by means of sodium borohydride in methanol and at room temperature.

If a compound of the general formula VII contains a double bond in the radical $R_6$, this bond can be hydrogenated at the same time, in the presence of catalytically activated hydrogen, during the course of the reaction with hydrogen.

(e) For the preparation of compounds of the general formula I in which $R_2$ represents one of the saturated radicals mentioned initially:
Hydrogenating a compound of general formula

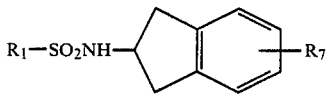

(VIII)

in which
$R_1$ is as defined initially and
$R_7$ represents one of the unsaturated radicals mentioned initially for $R_2$.

The hydrogenation is carried out in a suitable solvent, such as methanol, ethanol, dioxan, ethyl acetate or glacial acetic acid, by means of catalytically activated hydrogen or by means of nascent hydrogen at temperatures between 0° and 50° C., preferably at room temperature. In the course of this, a carbonyl group which may be present in the radical $R_7$ can at the same time be converted into a hydroxymethylene group.

For the preparation of a compound of the general formula I in which $R_2$ contains a carbonyl group, the reaction is preferably carried out in the presence of zinc/glacial acetic acid and at room temperature.

(f) For the preparation of compounds of general formula I in which $R_2$ represents a pyridazinone ring:
Reacting a compound of the general formula

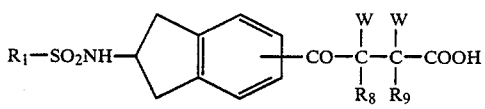

(IX)

in which
$R_1$ is as defined initially,
$R_8$ represents a hydrogen atom or an alkyl group having 1 to 3 carbon atoms,
$R_9$ represents a hydrogen atom, an alkyl group having 1 to 3 carbon atoms or an alkoxycarbonyl group having a total of 2 to 4 carbon atoms, it being possible, however, for only one of the radicals $R_8$ or $R_9$ to represent an alkyl group having 1 to 3 carbon atoms, and
each W represents a hydrogen atom or they represent together a further bond, or reactive derivatives thereof, such as esters, amides or halides thereof, with hydrazine.

The reaction is suitably carried out in a solvent, such as methanol, ethanol, isopropanol, glacial acetic acid or propionic acid, and/or in an excess of hydrazine or hydrazine hydrate at temperatures between 0° and 200° C., for example at temperatures between 20° and 150° C., but preferably at the boiling point of the reaction mixture, and, if appropriate, in the presence of an acid, such as sulphuric acid or p-toluenesulphonic acid, as a condensation agent. The reaction can, however, also be carried out in the absence of a solvent.

(g) For the preparation of compounds of the general formula I in which $R_2$ represents the carboxyl group:
Reacting a compound of the general formula

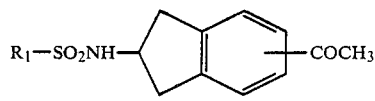

(X)

in which
$R_1$ is as defined initially with a hypohalite.

The haloform reaction is preferably carried out in an aqueous solvent, such as water/tetrahydrofuran or water/dioxan, at temperatures between 0° and 50° C., but preferably at room temperature. In this reaction it is suitable to prepare the hypohalite employed, for example sodium hypobromite, in the reaction mixture by reacting bromine with sodium hydroxide solution.

(h) For the preparation of compounds of the general formula I in which $R_2$ represents the hydroxycarbonylmethyl group:
Reacting a compound of the general formula

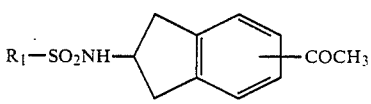

(X)

in which
$R_1$ is as defined initially, with sulphur in the presence of an amine, and subsequently saponifying.

The Willgerodt reaction is carried out using sulphur in the presence of an amine, such as morpholine, at elevated temperatures, for example at temperatures between 100° and 150° C. The subsequent hydrolysis of the amine thus obtained is carried out in trichloroacetic acid or in the presence of a base, such as sodium hydroxide or potassium hydroxide, in a suitable solvent, such as water, water/methanol, ethanol, water/ethanol, water/isopropanol or water/dioxane, at temperatures between $-10°$ and 120° C., for example at temperatures between room temperature and the boiling point of the reaction mixture.

(i) For the preparation of compounds of the general formula I in which $R_2$ represents a 2-hydroxycarbonylethenyl or 2-alkoxycarbonyl-ethenyl group:
Reacting a compound of the general formula

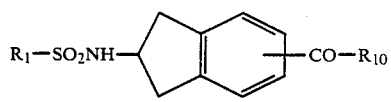

(XI)

in which
$R_1$ is as defined initially and $R_{10}$ represents a hydrogen atom or an alkyl group having 1 to 3 carbon atoms, with an appropriate trialkyl phosphonoacetate and, if necessary, subsequently hydrolysing the product.

The reaction is carried out in the presence of a base, such as potassium tert.-butylate or sodium hydride, and in a solvent, such as dimethylformamide, at temperatures of between 25° and 100° C., preferably at temperatures between 50° and 75° C.

The hydrolysis which may subsequently be necessary is suitably carried out either in the presence of an acid, such as hydrochloric acid, sulphuric acid, phosphoric acid or trichloroacetic acid, or in the presence of a base, such as sodium hydroxide or potassium hydroxide, in a suitable solvent, such as water, water/methanol., ethanol, water/ethanol, water/isopropanol or water/dioxan, at temperatures between −10° and 120° C., for example at temperatures between room temperature and the boiling point of the reaction mixture.

(k) For the preparation of compounds of the general formula I in which $R_2$ represents a 4,5-dihydropyridazin-3-one or pyridazin-3-one ring which is optionally substituted in the 4-position or 5-position by an alkyl group:

Decarboxylating a compound, which has optionally been formed in the reaction mixture, of the general formula

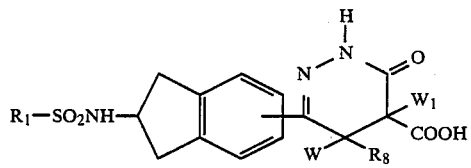

(XII)

in which
$R_1$ is as defined initially,
$R_8$ is a hydrogen atom or an alkyl group having 1 to 3 carbon atoms,
W denotes a hydrogen atom and
$W_1$ denotes a hydrogen atom or an alkyl group having 1 to 3 carbon atoms, or W and $W_1$ together denote a further bond.

The decarboxylation is suitably carried out in a suitable solvent, such as methanol/water, ethanol/water or dioxan/water, and preferably in the presence of an acid, such as hydrochloric acid or sulphuric acid, at temperatures between 0° and 150° C., preferably at temperatures between 50° and 100° C. In this reaction it is suitable to use as starting material a corresponding carboxylic acid derivative of the general formula XII, preferably a corresponding ester, such as the methyl, ethyl, isopropyl or benzyl ester, for the preparation of a compound of the general formula XII by hydrolysis in the reaction mixture in the presence of an acid, such as hydrochloric acid or sulphuric acid, or in the presence of a base, such as sodium hydroxide or potassium hydroxide. The decarboxylation can, however, also be carried out by heating in the absence of a solvent.

(1) For the preparation of compounds of the general formula I in which $R_2$ represents one of the oxobutyric acid ester radicals mentioned initially:

Reacting a compound of the general formula

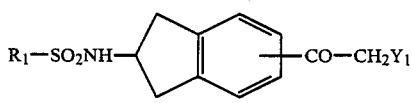

(XIII)

in which
$R_1$ is as defined initially and
$Y_1$ represents a nucleophilic leaving group, such as a halogen atom, for example a chlorine, bromine or iodine atom, or $Y_1$, together with the adjacent hydrogen atom, represents an oxygen atom, with a compound of the general formula

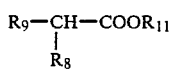

(XIV)

in which
$R_8$ represents a hydrogen atom or an alkyl group having 1 to 3 carbon atoms,
$R_9$ represents a hydrogen atom, an alkyl group having 1 to 3 carbon atoms or an alkoxycarbonyl group having a total of 2 to 4 carbon atoms, it being possible, however, for only one of the radicals $R_8$ or $R_9$ to represent an alkyl group having 1 to 3 carbon atoms, or, if $R_9$ represents an alkoxycarbonyl group having a total of 2 to 4 carbon atoms, $R_8$, together with the CH group, represents a methylene group and
$R_{11}$ represents alkyl group having 1 to 3 carbon atoms, in the presence of a base.

The reaction is preferably carried out in a solvent, such as acetone, dimethylformamide or dimethyl sulphoxide, in the presence of a base, such as sodium hydroxide, Potassium hydroxide, sodium hydride, potassium tert.-butylate or piperidine/pyridine, it being also possible to use piperidine/pyridine as the solvent, at temperatures between 0° and 100° C., preferably at temperatures between 20° and 50° C.

If a compound of the general formula I in which $R_2$ represents or contains a hydroxycarbonyl group is obtained in accordance with the invention, this group can be converted by esterification into a corresponding alkoxycarbonyl compound.

The subsequent esterification is suitably carried out in a solvent, for example in an excess of the alcohol employed, such as methanol, ethanol or isopropanol, in the presence of an agent which activates the acid, such as thionyl chloride or hydrogen chloride gas, and at temperatures between 0° and 180° C., but preferably at the boiling point of the reaction mixture.

The resulting compounds of the general formula I can also be resolved into their enantiomers. Thus the resulting compounds of the general formula I containing only one optically active centre can be resolved into their optical antipodes by methods which are in themselves known (see Alinger N. L. and Elich W. L. in "Topics in Stereochemistry", Vol. 6, Wiley Interscience, 1971), for example by recrystallisation from an optically active solvent or by reaction with an optically active substance, in particular bases, which forms salts with the racemic compound, and separating, for example on the basis of different solubilities, the mixture of salts obtained in this manner into the diastereomeric salts, from which the free antipodes can be liberated by the action of suitable agents. Examples of optically active bases which are particularly customary are the D-form and L-forms of α-phenyl-ethylamine or cinchonidine.

Furthermore, the resulting compounds of the general formula I containing at least 2 asymmetric carbon atoms can be separated into their diastereomers by virtue of their physico-chemical differences in accordance with methods which are in themselves known, for example by chromatography and/or fractional crystallisation. A pair of enantiomers obtained in this way can then be resolved into its optical antipodes as described above. If, for example, a compound of the general formula I contains two optically active carbon atoms, the corresponding (R R′, S S′)-forms and (R S′, S R′)-forms are obtained.

Furthermore, the new compounds of the general formula I thus obtained can, if they contain a carboxyl group, then be converted, into their addition salts with inorganic or organic bases, in particular into their physiologically acceptable addition salts for pharmaceutical use. Examples of bases suitable in this regard are sodium hydroxide, potassium hydroxide, cyclohexylamine, ethanolamin, diethanolamine and triethanolamine.

The compounds of the general formulae II to XIV which are used as starting materials are obtained by processes known from the literature or are known from the literature.

A compound of the general formula II which is used as a starting material is obtained from a corresponding N-acylaminoindanyl compound by Friedel-Crafts acylation, subsequent deacylation and, if appropriate, subsequent reduction, hydrolysis and/or esterification.

The compounds of the general formulae IV, V, VII, VIII, IX, X and XI which are used as starting materials are obtained by reacting an appropriate amino compound with an appropriate sulphonyl halide.

A compound of the general formula XII which is used as a starting material is obtained by reacting an appropriate oxo compound with hydrazine.

One compound of the general formula XIII which is used as starting materials is obtained by halogenating an appropriate acetyl compound.

As already mentioned initially, the new compounds and their physiologically acceptable addition salts with inorganic or organic bases exhibit valuable pharmacological properties, in particular an antithrombotic action and an inhibitory action on the aggregation of platelets. In addition, they are also thromboxane antagonists. By virtue of their inhibitory action on phosphodiesterase, the new piperidazinones of the general formula I also exhibit an inhibitory action on tumour metastasis.

The biological properties of, for example, the following new compounds:

A = 4-[2-p-Chlorobenzenesulphonamido-indan-5-yl]-4-oxobutyric acid,
B = 4-[2-p-Toluenesulphonamido-indan-5-yl]-4-oxobutyric acid,
C = [2-p-Chlorobenzenesulphonamido-indan-5-yl]-acetic acid,
D = 4-[2-p-Chlorobenzenesulphonamido-indan-5-yl]-butyric acid,
E = 6-[2-p-Toluenesulphonamido-indan-5-yl]-4,5-dihydropyridazin-3(2H)-one,
F = 6-[2-o-Methoxybenzenesulphonamido-indan-5-yl]-4,5-d ihydro-pyridazin-3(2H)-one and
G = 5-Methyl-6-[2-benzenesulphonamido-indan-5-yl]-4,5-d ihydropyridazin-3(2H)-one, are tested as follows:

1. Antithrombotic action
Method employed

Thrombocyte aggregation is measured in the platelet-rich plasma of healthy test persons by the method of BORN and CROSS (J. Physiol. 170, 397 (1964)). In order to inhibit clotting, 3.14% sodium citrate is added to the blood in a volume ratio of 1:10.

Collagen-induced aggregation

After the substance initiating aggregation has been added, the progress of the decrease in the optical density of the platelet suspension is measured and recorded photometrically. The rate of aggregation is calculated from the angle of inclination of the density curve. The point in the curve at which light transmittance is at a maximum is used to calculate the "optical density".

The amount of collagen selected is as small as possible, but sufficient to give a reaction curve which proceeds irreversibly. The commercially available collagen made by Hormonchemie, Munich, is used. Before the collagen is added, the plasma is in each case incubated with the substance for 10 minutes at 37° C.

An $ED_{50}$ which corresponds to a 50% change in the "optical density" in the sense of inhibition of aggregation is calculated graphically from the numerical values obtained.

The results found are shown in the following Table:

| Substance | $ED_{50}$ [μmol/l] |
| --- | --- |
| A | 0.37 |
| B | 0.5 |
| C | 0.27 |
| D | 0.8 |
| E | 2.85 |
| F | 0.35 |
| G | 0.25 |

2. Acute toxicity

The acute toxicity of the substances to be investigated was approximated on groups of 10 mice after the oral administration of a single dose (observation time: 14 days):

| Substance | Approximated acute toxicity |
| --- | --- |
| A | 1,000 mg/kg (0 out of 10 animals died) |
| B | 1,000 mg/kg (0 out of 10 animals died) |
| C | 1,000 mg/kg (0 out of 10 animals died) |
| D | 1,000 mg/kg (0 out of 10 animals died) |
| E | 500 mg/kg (0 out of 10 animals died) |
| F | 500 mg/kg (0 out of 10 animals died) |
| G | 500 mg/kg (0 out of 10 animals died) |

By virtue of their pharmacological properties, the new compounds and their physiologically acceptable addition salts are suitable for the treatment and prophylaxis of thrombo-embolic diseases, such as coronary infarction, cerebral infarction, so-called transient ischaemic attacks and amaurosis fugax, for prophylaxis of arteriosclerosis and for the prophylaxis of metastasis.

The dosage required to achieve an appropriate effect is suitably 0.3 to 4 mg/kg of body weight, preferably 0.3 to 2 mg/kg of body weight, twice to four times a day. The compounds of the general formula I, prepared in accordance with the invention, can be incorporated for this purpose into customary pharmaceutical formulations, such as tablets, coated tablets, capsules, powders, suspensions or suppositories, optionally in combination with other active substances and together with one or more inert, customary excipients and/or diluents, for example maize starch, lactose, cane sugar, microcrystalline cellulose, magnesium stearate, polyvinylpyrrolidone, citric acid, tartaric acid, water, water/ethanol, water/glycerol, water/sorbitol, water/polyethylene glycol, propylene glycol, cetyl stearyl alcohol, carboxymethyl cellulose or substances containing fat, such as solid fat, or suitable mixtures thereof.

The following Examples are intended to illustrate the invention in greater detail:

EXAMPLE A

Methyl 4-(2-amino-indan-5-yl)-4-oxobutyrate 1. 4-(2-Acetamido-indan-5-y])-4-oxobutyric acid
137.3 g (1.03 mol) of anhydrous aluminium chloride and 34.2 g (0.34 mol) of succinic anhydride are suspended in 500 ml of ethylene chloride and 54.5 g (0.311 mol) of 2-acetamido-indane are introduced at room temperature, with vigorous stirring. The mixture is stirred at room temperature for a further 2 hours, ice and 150 ml of concentrated hydrochloric acid are added, and the ethylene chloride is removed by steam distillation. On cooling, 4-(2-acetamido-indan-5-yl)-4-oxobutyric acid crystallises out from the aqueous solution. The acid is purified by being dissolved in 2N sodium hydroxide solution, the solution is filtered and the acid is reprecipitated by means of hydrochloric acid.

Yield: 74.5 g (87% of theory),
Melting point: 173°–177° C.
IR spectrum (in KBr): NH at 3380 cm$^{-1}$, CO at 1725+1680 cm$^{-1}$, amide-II at 1530 cm$^{-1}$ and CO at 1640 cm$^{-1}$.

2. Methyl 4-(2-amino-indan-5-yl)-4-oxobutyrate hydrochloride 74.5 g of 4-(2-acetylamino-indan-5-yl)-4-oxobutyric acid are boiled for 6 hours under reflux with semi-concentrated hydrochloric acid. The mixture is evaporated in vacuo and the residue is dried by boiling with toluene in a water separator. The 4-(2-amino-indan-5-yl)-4-oxobutyric acid hydrochloride which remains is esterified by being suspended in 600 ml of methanol. Hydrogen chloride gas is passed in with stirring until saturation is reached. The mixture is then cooled and the precipitated reaction product is filtered off with suction.

Yield: 58.6 g (76.5% of theory),
Melting point: 198°–200° C.
$C_{14}H_{18}ClNO_3$ (283.76) Calculated: C 59.26 H 6.39 N 4.94 Cl 12.49 Found: 59.20 6.59 4.95 12.63

Example B 6-(2-amino-indan-5-yl)-4,5-dihydro-pyridazin-3(2H)-one 8.5 g (0.17 mol) of 99% hydrazine hydrate are added to 10.0 g (0.035 mol) of methyl 4-(2-amino-indan-5-yl)-4-oxobutyrate hydrochloride in glacial acetic acid and the mixture is boiled for 30 minutes. The mixture is evaporated in vacuo, the residue is dissolved in water and the reaction product is precipitated by neutralisation with sodium hydroxide.

Yield: 6.5 g (80% of theory),
Melting point: 203°–205° C. (decomp.)
$C_{13}H_{15}H_3O$ (229.28) Calculated: C 68.10 H 6.59 N 18.33 Found: 68.14 6.41 18.35

EXAMPLE C (2-Benzenesulphonamido-indan-5-yl) methyl ketone 29.6 g (0.22 mol) of anhydrous aluminium chloride are suspended in 250 ml of ethylene chloride and 10.5 g (0.133 mol) of acetyl chloride and 24.2 g (0.0885 mol) of 2-(benzenesulphonamido)-indane are added successively. After the mixture has been stirred for approx 3 hours at room temperature, it is decomposed with ice and concentrated hydrochloric acid. The reaction product is obtained by concentrating the organic phase and subsequently crystallising the product from cyclohexane/ethyl acetate.

Yield: 21.8 g (78% of theory),
Melting point: 119°–121° C.
NMR spectrum (in $CDCl_3$–$CD_3OD$): CH: multiplet at 4.1 ppm, 4 aliphatic H; multiplet at 2.6 to 3.4 ppm, $CH_3CO$ at 2.55 ppm.

EXAMPLE D

Methyl 3-methyl-4-(2-amino-indan-5-yl)-4-oxobutyrate hydrochloride 1. 2-Acetamido-5-(2-chloropropionyl)-indane 19.0 g (0.147 mol) of 2-chloropropionyl chloride, followed by 25 g (0.14 mol) of 2-acetylamino-indane are added to a suspension of 40 g (0.3 mol) of anhydrous aluminium chloride. After the mixture has been stirred for 3 hours, it is decomposed with ice and concentrated hydrochloric acid. The reaction product is obtained by concentrating the organic phase.

Yield: 37 g (100%)
Oil, RF-value: 0.2 (silica gel polygram plate; 1:1 cyclohexane/ethyl acetate).

2. 3-Methyl-4-(2-acetamido-indan-5-Yl)-4-oxobutyric acid 17.8 g (0.154 mol) of potassium tert.-butanolate are added, with stirring, to a solution of 25 g (0.154 mol) of diethyl malonate in 40 ml of dimethyl sulphoxide; after a clear solution has been formed, 38.7 g (0.14 mol) of 2-acetylamino-5-(2-chloropropionyl)-indane, dissolved in 30 ml of dimethyl sulphoxide, are added. The mixture is stirred for 18 hours at room temperature, water is added and the ethyl 2-carboethoxy-3-methyl-4-oxo-4-(2-acetamido-indan-5-yl)-butyrate is extracted with ethyl acetate. The reaction product is obtained as an oil after evaporation. 160 ml of 4N sodium hydroxide solution are added to this oil, without further purification, and the mixture is stirred for 22 hours at room temperature. A clear solution is formed after about 5 hours. The mixture is washed with methylene chloride and the 2-carboxy-3-methyl-4-oxo-(2-acetamido-indan-5-yl)-butyric acid is precipitated with hydrochloric acid. It is extracted with ethyl acetate and obtained in the form of an oil after evaporating the extract.

Yield: 46.6 g (99.8).
RF value: 0.1 (silica gel-polygram plates; ethyl acetate as mobile phase).
This oil is decarboxylated by mixing with 40 ml of diethylene glycol dimethyl ether and heating for 1.5 hours at 120°–140° C., whereupon a vigorous evolution of $CO_2$ takes place. The mixture is diluted with water, rendered alkaline with sodium hydroxide solution and washed with methylene chloride, and the 3-methyl-4-[2-acetamido-indan-5-yl]-4-oxobutyric acid is precipitated in the form of an oil which slowly solidifies.

Yield: 31 g (77% of theory).

3. Methyl 3-methyl-4-(2-amino-indan-5-Yl)-4-oxobutyrate hydrochloride

In order to hydrolyse the acetylamino group, 31 g of the above compound are boiled for 8 hours with 120 ml of semi-concentrated hydrochloric acid. The mixture is evaporated in vacuo and the 3-methyl-4-oxo-(2-amino-indan-5-yl)-4-butyric acid hydrochloride which remains is dried. It is dissolved in 400 ml of methanol and hydrogen chloride gas is then passed in until saturation is reached and the mixture is allowed to stand overnight. It is evaporated in vacuo and the residue is chromatographed over 250 g of silica gel, using 96:4 chloroform/methanol as the mobile phase. This gives crystalline methyl 3-methyl-4-(2-amino-indan-5-yl)-4-oxobutyrate hydrochloride.

Yield: 15.5 g (43% of theory),
Melting point: 169°–173° C.
$C_{15}H_{19}NO_3$ x HCl (297.78) Calculated: C 60.50 H 6.77 N 4.70 Cl 11.91 Found: 60.70 6.55 4.81 12.07

EXAMPLE E

2-Benzenesulphonamido-indane

A layer of 180 ml of semi-saturated potassium carbonate solution is placed under 20 g (0.118 mol) of 2-aminoindane hydrochloride in 100 ml of dioxan, and 26.0 g (0.142 mol) of benzenesulphonyl chloride are then added dropwise, with vigorous stirring. Stirring is continued for a further 2 hours, the precipitate of the salt is filtered off with suction and the reaction product is isolated from the dioxan phase. It is recrystallised from 150 ml of cyclohexane and 30 ml of ethyl acetate.

Yield: 27.5 g (85.2% of theory),
Melting point: 101°–102° C.

The following are obtained analogously:

2-(p-Chlorobenzenesulphonamido)-indane

Yield: 71% of theory,
Melting point: 141°–142° C.
IR spectrum (in methylene chloride): NH at 3360 $cm^{-1}$, $SO_2$ at $1160+1340$ $cm^{-1}$

2-(o-Toluenesulphonamido)-indane

Yield: 86% of theory,
Melting point: 72°–74° C.
IR spectrum (in methylene chloride): NH at 3360 $cm^{-1}$, $SO_2$ at $1155+1330$ $cm^{-1}$

EXAMPLE F

Methyl 4-(2-amino-indan-5-yl)-butyrate 3 ml of perchloric acid and 3 g of 10% palladium-on-charcoal are added to 15 g (52.8 mmol) of methyl 4-(2-amino-indan-5-yl)-4-oxobutyrate in 200 ml of glacial acetic acid and the mixture is hydrogenated at 50° C. and a hydrogen pressure of 5 bar. When the calculated amount of hydrogen has been absorbed, the catalyst is filtered off, the filtrate is evaporated, sodium hydroxide is added to the residue and the reaction product is extracted with ether. After drying and evaporation, the desired product is obtained in the form of an oil.

Yield: 9 g (73% of theory),
Rf value: 0.5 (silica gel-polygram plates made by Merck; 20:50:20:10 toluene/dioxan/methanol/ammonia).
IR spectrum (in methylene chloride): $OCH_3$ at 2840 $cm^{-1}$, CO at 1735 $cm^{-1}$.
NMR spectrum (in $CDCl_3$, $CD_3OD$): CH: multiplet at 3.7 ppm, 10 aliphatic H: multiplet at 1.7 to 3.4 ppm, $OCH_3$ at 3.6 ppm.

EXAMPLE G

(2Acetamido-indan-5-yl) methyl ketone 24.4 g (0.31 mol) of acetyl chloride, followed by 35.5 g (0.20 mol) of 2-acetamido-indane are added, with stirring, to a suspension of 68 g (0.51 mol) of anhydrous aluminium chloride in 350 ml of ethylene chloride. In the course of this the reaction temperature rises to approx. 50° C. Stirring is continued for a further 3 hours, the product is decomposed by means of ice and concentrated hydrochloric acid, and the organic phase is separated off and evaporated.

Yield: 42.0 g (96% of theory).
A sample is recrystallised from isopropanol.
Melting point: 143°–145° C.
$C_{13}H_{15}NO_2$ (217.27) Calculated: C 71.87 H 6.96 N 6.45 Found: 71.81 6.67 6.56

EXAMPLE H

Methyl (2-amino-indan-5-yl)-acetate 23.6 g (0.108 mol) of (2-acetamido-indan-5-yl) methyl ketone, 5.45 g (0.17 mol) of sulphur and 22 g (0.25 mol) of morpholine are heated to boiling for 6.5 hours. After cooling, ethyl acetate is added. (2-Acetamido-indan-5-yl)-acetic acid thiomorpholide is obtained in crystalline form. It is purified by crystallisation from isopropanol.

Yield: 29.7 g (86% of theory).
Melting point: 171°–174° C.

This thiomorpholide is boiled for 16 hours with 37 g (0.56 mol) of potassium hydroxide in 50 ml of water and 50 ml of ethanol. The mixture is evaporated, excess hydrochloric acid is added to the residue, and the mixture is again evaporated to dryness. The residue is digested with methanol, potassium chloride is filtered off with suction and hydrogen chloride gas is passed into the filtrate until saturation is reached. After standinq overnight, the mixture is evaporated. The hydrochloride of methyl (2-amino-indan-5-yl)-acetate is triturated with acetone and ether and is filtered off with suction.

Yield: 13.9 g (62% of theory),
Melting point: 120°–125° C.
$C_{12}H_{16}ClNO_2$ (241.72) Calculated: Cl 14.67 N 5.79 Found: 14.65 5.87

EXAMPLE I

Methyl 2-(2-amino-indan-5-yl)-propionate hydrochloride (a) 1-(2-Acetamido-indan-5-yl)-1-ethanol A solution of 4.6 g (0.12 mol) of sodium borohydride in 25 ml of water is added to 24 g (0.11 mmol) of (2-acetamido-indan-5-yl) methyl ketone (Example G) in 200 ml of methanol at room temperature. After 2½ hours, the mixture is evaporated in vacuo and the residue is diluted with ice-water and acidified. The reaction product is extracted with 9:1 methylene chloride/methanol, the organic phase is dried, and the solvent is removed in vacuo.

Yield: 18.6 g (77% of theory),
Melting point: 127°–129° C.
IR spectrum (in methylene chloride): OH at 3610 $cm^{-1}$, CONH at 1670 and 1510 $cm^{-1}$.

(b) 1-(2-Acetamido-indan-5-yl)-1-chloroethane 25 g (0.11 mol) of 1-(2-acetamido-indan-5-yl)-1-ethanol are suspended in 280 ml of methylene chloride, and 15 g (0.12 mol) of thionyl chloride are added. A clear solution is formed. After 1 hour, this solution is neutralised by washing with a saturated solution of sodium bicarbonate. The desired reaction product is obtained after drying and evaporating.

Yield: 26.1 g (97% of theory),
Melting point: 102°–104° C.
$C_{13}H_{16}ClNO$ (237.73) Calculated: C 65.68 H 6.78 N 5.89 Cl 14.91 Found: 65.72 6.48 6.23 14.68
IR spectrum (in methylene chloride): NH at 3440 $cm^{-1}$, CONH at 1670 and 1510 $cm^{-1}$.

(c) 2-(2-Acetamido-indan-5-yl)-1-propionitrile 13.3 g (0.056 mol) of 1-(2-acetamido-indan-5-yl)-1-chloroethane are heated with 3.3 g (0.067 mol) of sodium cyanide in 45 ml of dimethyl sulphoxide for 7 hours at 70° C. 200 ml of water are added, and the mixture is extracted with ethyl acetate. The organic phase is dried and concentrated in vacuo.

Yield: 9.3 g (73% of theory), Oil, Rf-value: 0.5 (silica gel-polygram plates SIL G/UV made by Macherey- Nagel, Duren; mobile phase: 9:1 ethylene chloride/isopropanol).

(d) Methyl 2-(2-amino-indan-5-yl)-propionate hydrochloride

A solution of 12.5 g (0.05 mol) of 2-(2-acetamido-indan-5-yl)-propionitrile in 150 ml of methanol is saturated with hydrogen chloride gas. The mixture is then boiled for 40 hours. The solution is concentrated in vacuo. The residue is a crystalline material.

Yield: 10.0 g (79% of theory),

IR spectrum (in KBr): ester-CO at 1730 cm$^{-1}$.

EXAMPLE K (2-p-Toluenesulphonamido-indan-5-yl)chloromethylketone (a) 2-p-Toluenesulphonamido-indane Prepared analogously to Example E from 2-amino-indane hydrochloride and p-toluenesulphonyl chloride.

Yield: 90% of theory,

Melting point: 130°–132° C. (ethyl acetate/cyclohexane).

(b) (2-p-Toluenesulphonamido-indan-5-yl) chloromethyl ketone 25.4 g (0.19 mol) of anhydrous aluminium chloride are suspended in 80 ml of ethylene chloride and 11.1 g (0.095 mol) of chloroacetyl chloride are added. 22.8 g (0.079 mol) of 2-p-toluenesulphonamido-indane are then added and the mixture is stirred for 2 hours at room temperature. The product is then decomposed by means of ice and hydrochloric acid and the reaction product is isolated from the organic phase and recrystallised from ethyl acetate/cyclohexane.

Yield: 23.5 g (31.4% of theory),

Melting point: 132°–134° C.

$C_{18}H_{18}ClNO_3S$ (363.86) Calculated: C 59.42 H 4.99 N 3.85 Cl 9.75 S 8.81 Found: 59.22 4.86 3.58 10.00 9.03

The following is prepared analogously:

(2-p-Chlorobenzenesulphonamido-indan-5-yl) chloromethyl ketone

Yield: 91% of theory,

Melting point: 167°–170° C. (from ethylene chloride).

EXAMPLE 1

Methyl 4-(2-benzenesulphonamido-indan-5-yl)-4-oxobutyrate 6.4 g (22.5 mmol) of methyl 4-(2-amino-indan-5-yl)-4-oxobutyrate hydrochloride are suspended in 35 ml of pyridine and 5.0 g (25 mmol) of benzenesulphonyl chloride are added, followed by 2.7 g (27 mmol) of triethylamine. The mixture is stirred for 3 hours and evaporated in vacuo, hydrochloric acid is added and the reaction product is extracted by shaking with ethyl acetate. It is purified by chromatography over 350 g of silica gel, using 1:1 cyclohexane/ethyl acetate.

Yield: 8.6 g (99% of theory)

Oil, Rf-value: 0.4 (silica gel-polygram plates; 1:1 cyclohexane/ethyl acetate)

IR spectrum (in methylene chloride): NH at 3360 cm$^{-1}$, ester-CO at 1735 cm$^{-1}$, ketone-CO at 1680 cm$^{-1}$, SO$_2$ at 1155+1340 cm$^{-1}$.

NMR spectrum (in CDCl$_3$-CD$_3$OD): CH and 8 aliphatic H as multiplets at 4.1 and 2.6 to 3.4 ppm, OCH$_3$ at 3.7 ppm.

EXAMPLE 2

4-(2-Benzenesulphonamido-indan-5-yl)-4-oxobutyric acid 2.7 ml of 15N sodium hydroxide solution are added to 8.3 g (21.4 mmol) of methyl 4-[2-benzenesulphonamido-indan-5-yl]-4-oxobutyrate in 20 ml of ethanol and the mixture is boiled for 2 hours. The mixture is evaporated in vacuo, the residue is taken up in water, and the reaction product is precipitated with hydrochloric acid. It is crystallised from ethyl acetate/diisopropyl ether.

Yield: 134°–136° C.

$C_{19}H_{19}NO_5S$ (373.43) Calculated: C 61.11 H 5.13 N 3.75 S 8.59 Found: 61.20 5.37 3.76 8.81

EXAMPLE 3

Methyl 4-(2-p-fluorobenzenesulphonamido-indan-5-yl)-4-oxobutyrate

Prepared analogously to Example 1 from methyl 4-(2-amino-indan-5-yl)-4-oxobutyrate hydrochloride and p-fluorobenzenesulphonyl chloride in pyridine and triethylamine.

Yield: 80% of theory,

Melting point: 130°–132° C. (1:1 cyclohexane/ethyl acetate)

$C_{20}H_{20}FNO_5S$ (405.45) Calculated: C 59.25 H 4.97 N 3.45 S 7.91 Found: 59.01 5.10 3.39 8.16

EXAMPLE 4

4-(2-p-Fluorobenzenesulphonamido-indan-5-yl)-4-oxobutyric acid

Prepared analogously to Example 2 from methyl 4-(2-p-fluorobenzenesulphonamido-indan-5-yl)-4-oxobutyrate by hydrolysis with sodium hydroxide.

Yield: 75% of theory.

The substance crystallises from isopropanol in two modifications having melting points of 133°–135° C. and 174°–176° C.

$C_{19}H_{18}FNO_5S$ (391.42) Calculated: C 58.30 H 4.64 N 3.58 S 8.19 Substance of melting point 133°–135° C.: Found: C 58.02 H 4.60 N 3.56 S 8.21 Substance of melting point 174°–176° C.: Found: C 58.33 H 4.68 N 3.63 S 8.41

EXAMPLE 5

Methyl 4-(2-p-toluenesulphonamido-indan-5-yl)-4-oxobutyrate 6.0 g (21.1 mmol) of methyl 4-(2-amino-indan-5-yl)-4-oxobutyrate hydrochloride are suspended in 60 ml of chloroform and 5.0 g (25.3 mmol) of p-toluenesulphonyl chloride are added. 5.1 g (50 mmol) of triethylamine are added, with vigorous stirring, a clear solution being formed. After 20 hours at room temperature, the mixture is washed with water, the chloroform solution is evaporated and the residue is recrystallised from methanol.

Yield: 7.1 g (84% of theory),

Melting point: 108°–110° C.

$C_{21}H_{23}NO_5S$ (401.48) Calculated: C 62.83 H 5.77 N 3.49 S 7.99 Found: 62.70 5.70 3.45 7.80

EXAMPLE 6

4-(2-p-Toluenesulphonamido-indan-5-yl)-4-oxobutyric acid

Prepared analogously to Example 2 from methyl 4-(2-p-toluenesulphonamido-indan-5-yl)-4-oxobutyrate by hydrolysis with sodium hydroxide.

Yield: 72% of theory.

The substance crystallises from ethyl acetate in two modifications having melting points at 143°–145° C. and 161°–163° C.

$C_{20}H_{21}NO_5S$ (487.46) Calculated: C 62.20 H 5.46 N 3.62 S 8.27 Substance of melting point 143°–145° C.: Found: C 62.24 H 5.29 N 3.56 S 8.37 Substance of melting point 161°–163° C.: Found: C 62.30 H 5.29 N 3.64 S 8.37

EXAMPLE 7

Methyl 4-(2-o-methoxybenzenesulphonamido-indan-5-yl)-4-oxobutyrate

Prepared analogously to Example 5 from methyl 4-(2-amino-indan-5-yl)-4-oxobutyrate hydrochloride and o-methoxybenzenesulphonyl bromide in chloroform in the presence of triethylamine.

Yield: 90% of theory,

Melting point: 115°–119° C.

NMR spectrum (in $CDCl_3$-$CD_3OD$): CH and 8 aliphatic H as multiplets at 4.1 and 2.6 to 3.4 ppm; two $OCH_3$ at 3.7 and 3.9 ppm

EXAMPLE 8

4-(2-o-Methoxybenzenesulphonamido-indan-5-yl)-4-oxobutyric acid

Prepared analogously to Example 2 from methyl 4-(2-o-methoxybenzenesulphonamido-indan-5-yl)-4-oxobutyrate by hydrolysis with sodium hydroxide.

Yield: 59% of theory,

Melting point: 148°–150° C. (ethylene chloride diisopropyl ether)

$C_{20}H_{21}NO_6S$ (403.46) Calculated: C 59.54 H 5.25 N 3.47 S 7.95 Found: 59.70 5.24 3.39 8.18

EXAMPLE 9

Methyl 4-(2-p-methoxybenzenesulphonamido-indan-5-yl)-4-oxobutyrate

Prepared analogously to Example 5 from methyl 4-(2-amino-indan-5-yl)-4-oxobutyrate hydrochloride and p-methoxybenzenesulphonyl chloride in chloroform in the presence of triethylamine.

Yield: 86% of theory,

Melting point: 101°–103° C. (methanol)

$C_{21}H_{23}NO_6S$ (417.48) Calculated: C 60.42 H 5.55 N 3.36 S 7.68 Found: 60.30 5.47 3.52 7.90

EXAMPLE 10

4-(2-p-Methoxybenzenesulphonamido-indan-5-yl)-4-oxobutyric acid

Prepared analogously to Example 2 from methyl 4-(2-p-methoxybenzenesulphonamido-indan-5-yl)-4-oxobutyrate by hydrolysis with sodium hydroxide.

Yield: 90% of theory,

Melting point: 131°–133° C. (ethylene chloride)

$C_{20}H_{21}NO_6S$ (403.46) Calculated: C 59.54 H 5.25 N 3.47 S 7.95 Found: 59.25 5.40 3.38 7.86

EXAMPLE 11

Methyl 3-methyl-4-(2-benzenesulphonamido-indan-5-yl)-4-oxobutyrate

Prepared analogously to Example 1 from methyl 3-methyl-4-(2-amino-indan-5-yl)-4-oxobutyrate hydrochloride and benzenesulphonyl chloride.

Yield: 98% of theory,

Oil, Rf-value: 0.8 (silica gel-polygram plates; mobile phase: 95:5 chloroform/methanol)

$C_{21}H_{23}NO_5S$ (401.48) Calculated: C 62.83 H 5.77 N 3.49 S 7.99 Found: 62.52 5.67 3.60 7.98

NMR spectrum (in $CDCl_3$-$CD_3OD$): CH and $CH(CH_3)$ multiplet at 4.0 ppm, 6 aliphatic H: multiplet at 2.2 to 3.4 ppm, $CH_3$: doublet at 1.15 ppm.

EXAMPLE 12

3-Methyl-4-(2-benzenesulphonamido-indan-5-yl)-4-oxobutyric acid

Prepared analogously to Example 2 from methyl 3-methyl-4-(2-benzenesulphonamido-indan-5-yl)-4-oxobutyrate by hydrolysis with sodium hydroxide.

Yield: 36% of theory,

Melting point: 101°–103° C.

$C_{20}H_{21}NO_5S$ (387.46) Calculated: N 3.62 S 8.27 Found: 3.40 8.04

EXAMPLE 13

Methyl 3-methyl-4-(2-p-fluorobenzenesulphonamido-indan-5-yl)-4-oxobutyrate

Prepared analogously to Example 1 from methyl 3-methyl-4-(2-amino-indan-5-yl)-4-oxobutyrate hydrochloride and p-fluorobenzenesulphonyl chloride.

Yield: 98% of theory,

Oil, Rf-value: 0.7 (polygram-silica gel plates; mobile phase: 95:5 chloroform/methanol)

$C_{19}H_{18}FNO_5S$ (391.42) Calculated: C 58.30 H 4.64 N 3.58 S 8.19 Found: 58.33 4.68 3.63 8.41

NMR spectrum (in $CDCl_3$-$CD_3OD$): CH and $CH(CH_3)$: multiplet at 4.0 ppm, 6 aliphatic H: multiplet at 2.2 to 3.4 ppm, $OCH_3$ at 3.65 ppm.

EXAMPLE 14

3-Methyl-4-(2-p-fluorobenzenesulphonamido-indan-5-yl)-4-oxobutyric acid

Prepared analogously to Example 2 from methyl 3-methyl-4-(2-p-fluorobenzenesulphonamido-indan-5-yl)-4-oxobutyrate by hydrolysis with sodium hydroxide.

Yield: 69% of theory,

Melting point: 155°–157° C. (toluene/ethyl acetate)

$C_{20}H_{20}FNO_5S$ (405.45) Calculated: C 59.25 H 4.97 N 3.45 S 7.91 Found: 59.00 5.14 3.36 8.17

EXAMPLE 15

Methyl 3-methyl-4-(2-p-toluenesulphonamido-indan-5-yl)-4-oxobutyrate

Prepared analogously to Example 1 from methyl 3-methyl-4-(2-amino-indan-5-yl)-4-oxobutyrate hydrochloride and p-toluenesulphonyl chloride.

Yield: 70% of theory,

Melting point: 112°–115° C. (100:5 diisopropyl ether/ethyl acetate)

$C_{22}H_{25}NO_5S$ (415.51) Calculated: C 63.60 H 6.06 N 3.37 S 7.72 Found: 63.32 5.97 3.49 7.54

EXAMPLE 16

3-Methyl-4-(2-p-toluenesulphonamido-indan-5-yl)-4-oxobutyric acid

Prepared analogously to Example 2 from methyl 3-methyl-4-(2-p-toluenesulphonamido-indan-5-yl)-4-oxobutyrate by hydrolysis with sodium hydroxide.

Yield: 73% of theory,
Melting point: 137°–139° C. (from toluene/ethyl acetate)
$C_{21}H_{23}NO_5S$ (401.48) Calculated: C 62.83 H 5.77 N 3.49 S 7.99 Found: 63.00 5.68 3.47 8.04

EXAMPLE 17

4-(2-p-Chlorobenzenesulphonamido-indan-5-yl)-4-oxobutyric acid 38.5 g (0.289 mol) of anhydrous aluminium chloride and 12.4 g (0.124 mol) of succinic anhydride are suspended in 250 ml of ethylene chloride and 25.4 g (0.082 mol) of 2-p-chlorobenzenesulphonamido-indane are then added, with vigorous stirring. In the course of this, a clear solution is formed. After 3 hours, the product is decomposed by means of ice and hydrochloric acid, and the reaction product is isolated from the organic phase. It is recrystallised from glacial acetic acid.

Yield: 13.8 g (41% of theory),
Melting point: 148°–150° C.
$C_{19}H_{18}ClNO_5S$ (407.87) Calculated: C 55.95 H 4.45 N 3.43 Cl 8.69 S 7.86 Found: 55.91 4.37 3.51 8.90 7.79

EXAMPLE 18

4-(2-o-Toluenesulphonamido-indan-5-yl)-4-oxobutyric acid

Prepared analogously to Example 17 from 2-(o-toluenesulphonamido)-indane and succinic anhydride.

Yield: 40% of theory,
Melting point: 110°–112° C. (cyclohexane/ethyl acetate)
$C_{20}H_{21}NO_5S$ (387.46) Calculated: C 62.00 H 5.46 N 3.62 S 8.28 Found: 62.17 5.61 3.53 8.41

EXAMPLE 19

4-(2-o-Toluenesulphonamido-indan-5-yl)-4-oxobutyrate 17.9 g (0.15 mol) of thionyl chloride are added at $-45°$ C. to 42.7 g (0.1 mol) of 4-(2-o-toluenesulphonamido-indan-5-yl)-4-oxobutyric acid in 100 ml of methanol. The mixture is allowed to stand at room temperature for some hours and is evaporated in vacuo, and the residue is chromatographed over silica gel using 1:1 cyclohexane/ethyl acetate. Fractions having an Rf-value of 0.6 (silica gel-polygram plates; 1:1 cyclohexane/ethyl acetate) are combined and evaporated. The reaction product is obtained in the form of an oil.

Yield: 23 g (57% of theory),
$C_{21}H_{23}NO_5S$ (401.48) Calculated: N 3.49 S 7.99 Found: 3.31 7.93

IR spectrum (in methylene chloride): NH at 3370 $cm^{-1}$, ester-CO at 1735 $cm^{-1}$, ketone-CO at 1675 $cm^{-1}$, $SO_2$ at $1160+1330$ $cm^{-1}$.

EXAMPLE 20

4-(2-Benzenesulphonamido-indan-5-yl)-4-oxobutyric acid

Prepared analogously to Example 17 from 2-benzenesulphonamido-indane and succinic anhydride.

Yield: 38% of theory,
Melting point: 131°–134° C. (diisopropyl ether)
$C_{19}H_{19}NO_5S$ (373.43) Calculated: C 61.11 H 5.13 N 3.75 S 8.59 Found: 61.20 5.37 3.76 8.81

EXAMPLE 21

6-(2-p-Fluorobenzenesulphonamido-indan-5-yl)-4,5-dihydro-pyridazin-3(2H)-one 2.9 g (12.6 mmol) of 6-(2-amino-indan-5-yl)-4,5-dihydropyridazin-3(2H)-one are dissolved in a mixture of 30 ml of dioxan and 10 ml of acetone, and 1.42 g (14 mmol) of triethylamine and 2.8 g of p-fluorobenzenesulphonyl chloride are added. After 2 hours, the mixture is evaporated, water is added to the residue, and the reaction product is filtered off with suction and recrystallised from glacial acetic acid.

Yield: 72% of theory,
Melting point: 209°–211° C.
$C_{19}H_{18}FN_3O_3S$ (387.43) Calculated: C 58.90 H 4.68 N 10.85 S 8.28 Found: 58.76 4.71 10.72 8.59

EXAMPLE 22

6-(2-p-Toluenesulphonamido-indan-5-yl)-4,5-dihydropyridazin-3(2H)-one

Prepared analogously to Example 21 from 6-(2-aminoindan-5-yl)-4,5-dihydro-pyridazin-3(2H)-one and p-toluenesulphonyl chloride.

Yield: 90% of theory,
Melting point: 185°–187° C. (n-propanol)
$C_{20}H_{21}N_3O_3S$ (383.47) Calculated: C 62.64 H 5.52 N 10.96 S 8.36 Found: 62.70 5.64 10.92 8.31

EXAMPLE 23

6-(2-Benzenesulphonamido-indan-5-yl)-4,5-dihydropyridazin-3(2H)-one 3.0 g (8 mmol) of 4-(2-benzenesulphonamido-indan-5-yl)-4-oxobutyric acid and 0.53 g (10.4 mmol) of 99% hydrazine hydrate in 12 ml of glacial acetic acid are boiled for 3 hours. The mixture is evaporated in vacuo, water is added to the residue, which is neutralised with sodium carbonate solution, and the reaction product is filtered off with suction and recrystallised from n-propanol.

Yield: 2.7 g (91% of theory),
Melting point: 178°–180° C.
$C_{19}H_{19}N_3O_3S$ (369.44) Calculated: C 61.77 H 5.18 N 11.37 S 8.68 Found: 61.74 5.37 11.21 8.95

EXAMPLE 24

6-(2-p-Chlorobenzenesulphonamido-indan-5-yl)-4,5-dihydro-pyridazin-3(2H)-one

Prepared analogously to Example 23 from 4-(2-p-chlorobenzosulphonamido-indan-5-yl)-4-oxobutyric acid and hydrazine hydrate in glacial acetic acid.

Yield: 38% of theory,
Melting point: 204°–206° C. (n-propanol)
$C_{19}H_{18}ClN_3O_3S$ (403.89) Calculated: C 56.50 H 4.49 N 10.40 Cl 8.78 S 7.94 Found: 56.60 4.56 10.29 8.64 7.82

EXAMPLE 25

6-(2-o-Methoxybenzenesulphonamido-indan-5-yl)-4,5-dihydro-pyridazin-3(2H)-one

Prepared analogously to Example 23 from 4-(2-o-methoxybenzenesulphonamido-indan-5-yl)-4-oxobutyric acid and hydrazine hydrate in glacial acetic acid.

Yield: 63% of theory,
Melting point: 224°-227° C. (ethylene chloride)
$C_{20}H_{21}N_3O_4S$ (399.47) Calculated: C 60.14 H 5.30 N 10.52 S 8.03 Found: 59.96 5.25 10.74 7.95

EXAMPLE 26

6-(2-p-Methoxybenzenesulphonamido-indan-5-yl)-4,5-dihydro-pyridazin-3(2H)-one 5.0 g (12 mmol) of methyl 4-(2-p-methoxybenzenesulphonamido-indan-5-yl)-4-oxobutyrate and 3.0 g (60 mmol) of 99% hydrazine hydrate in 25 ml of glacial acetic acid are boiled for 30 minutes. The mixture is evaporated, water is added to the residue, and the reaction product is filtered off with suction and recrystallised from n-propanol.

Yield: 4.3 g (90% of theory),
Melting point: 192°-193° C.
Calculated: C 60.14 H 5.30 N 10.52 S 8.03 Found: 59.61 5.17 10.82 8.06

EXAMPLE 27

6-(2-o-Toluenesulphonamido-indan-5-yl)-4,5-dihydropyridazin-3(2H)-one

Prepared analogously to Example 26 from methyl 4-(2-o-toluenesulphonamido-indan-5-yl)-4-oxobutyrate and hydrazine hydrate in glacial acetic acid.

Yield: 26% of theory,
Melting point: 191°-193° C. (n-propanol)
$C_{20}H_{21}N_3O_3S$ (383.47) Calculated: C 62.64 H 5.52 N 10.96 S 8.36 Found: 62.95 5.30 10.80 8.43

EXAMPLE 28

5-Methyl-6-(2-benzenesulphonamido-indan-5-yl)-4,5-dihydro-pyridazin-3(2H)-one

Prepared analogously to Example 23 from 3-methyl-4-(2-benzenesulphonamido-indan-5-yl)-4-oxobutyric acid and hydrazine hydrate in glacial acetic acid.

Yield: 80% of theory,
Melting point: 196°-198° C. (n-propanol)
Calculated: C 62.64 H 5.52 N 10.96 S 8.36 Found: 62.80 5.49 11.16 8.49

EXAMPLE 29

5-Methyl-6-(2-p-toluenesulphonamido-indan-5-yl)-4,5-dihydro-pyridazin-3(2H)-one

Prepared analogously to Example 26 from 3-methyl-4-(2-p-toluenesulphonamido-indan-5-yl)-4-oxobutyric acid and hydrazine hydrate in glacial acetic acid.

Yield: 83% of theory,
Melting point: 204°-207° C. (n-propanol)
$C_{21}H_{23}N_3O_3S$ (397.50) Calculated: C 63.46 H 5.83 N 10.57 S 8.07 Found: 63.80 5.92 10.48 8.01

EXAMPLE 30

(2-Benzenesulphonamido-indan-5-yl)-carboxylic acid 12.5 g (0.0795 mol) of bromine are added at −10° C. to a solution of 8.5 g (0.214 mol) of sodium hydroxide in 85 ml of water, and a solution of 5 g (0.015 mol) of 2-benzenesulphonamido-indan-5-yl methyl ketone in 20 ml of dioxan is then added with vigorous stirring. The mixture is stirred for 2 hours at room temperature, the excess bromine is destroyed by adding sodium bisulphite, the alkaline phase is washed with ether and acidified with hydrochloric acid, and the reaction product is extracted with methylene chloride. Evaporation leaves as residue 5.3 g of a resinous substance, which is recrystallised from glacial acetic acid and then from methanol/water.

Yield: 1.42 g (37% of theory),
Melting point: 180°-182° C.
$C_{16}H_{15}NO_4S$ (317.36) Calculated: C 60.55 H 4.76 N 4.41 S 10.10 Found: 60.60 4.58 4.38 10.23

EXAMPLE 31

(2-Benzenesulphonamido-indan-5-yl)-acetic acid 8.3 g (26 mmol) of (2-benzenesulphonamido-indan-5-yl) methyl ketone, 2.1 g (65 mmol) of sulphur and 5.7 g (65 mmol) of morpholine are heated at 135° C. for 2 hours. Ice and hydrochloric acid are added and (2-benzenesulphonamido-indan-5-yl)-acetic acid thiomorpholide is extracted with ethyl acetate. It is purified by chromatography over silica gel using 8:2 ethylene chloride/ethyl acetate, which gives 10.6 g (97% of theory) in the form of a resin. The product is then heated under reflux for 2.5 hours with 10 g of potassium hydroxide in 100 ml of water and 40 ml of ethanol. The mixture is concentrated in vacuo, the alkaline phase is washed with methylene chloride, and the reaction product is precipitated by means of hydrochloric acid. It is recrystallised from isopropanol and from ethyl acetate/diisopropyl ether.

Yield: 3.0 g (34% of theory),
Melting point: 109°-111° C.
$C_{17}H_{17}NO_4S$ (331.39) Calculated: C 61.62 H 5.17 N 4.23 S 9.68 Found: 61.65 5.30 4.16 9.55

EXAMPLE 32

Ethyl 3-(2-benzenesulphonamido-indan-5-yl)-crotonate 6.5 g (65.5 mmol) of potassium tert.-butanolate are added to a solution of 8.3 g (26.3 mmol) of (2-benzenesulphonamido-indan-5-yl) methyl ketone and 7.4 g (33 mmol) of triethyl phosphonoacetate in 30 ml of dimethylformamide and the mixture is heated at 60° C. for 11 hours. The mixture is diluted with water and acidified, and the reaction product is extracted with ether. It is purified by chromatography over silica gel using 1:1 cyclohexane/ethyl acetate.

Yield: 9.1 g (90% of theory),
Oil, Rf-value: 0.7 (silica gel-polygram plates; mobile phase cyclohexane/ethyl acetate).

EXAMPLE 33

3-(2-Benzenesulphonamido-indan-5-yl)-crotonic acid 3.4 ml of 15N sodium hydroxide solution are added to 9.1 g (23.6 mmol) of ethyl 3-(2-benzenesulphonamidoindan-5-yl)-crotonate in 100 ml of ethanol and the mixture is boiled for 1 hour. The sodium salt is precipitated on cooling. It is filtered off with suction and dissolved in water. The free acid is precipitated by adding hydrochloric acid and is recrystallised from isopropanol.

Yield: 2.1 g (25% of theory),
Melting point: 159°-161° C.
$C_{19}H_{19}NO_4S$ (357.43) Calculated: C 63.85 H 5.36 N 3.92 S 8.97 Found: 64.03 5.37 3.76 8.82

NMR spectrum (in CDCl$_3$-CD$_3$OD): 1 olefinic H at 6.15 ppm, CH$_3$ at 2.5 ppm, CH and 4 aliphatic H: multiplet at 4.1 and at 2.6–3.4 ppm.

EXAMPLE 34

Methyl 3-(2-benzenesulphonamido-indan-5-yl)-butyrate 3.2 g (8.95 mmol) of 3-(2-benzenesulphonamido-indan-5-yl)-crotonic acid in 50 ml of dioxan are hydrogenated in the presence of Raney nickel at room temperature under a hydrogen pressure of 3.5 bar. The mixture is filtered, the filtrate is evaporated, the residue is dissolved in 20 ml of methanol, and 1.5 ml of thionyl chloride are added dropwise at −50° C. The mixture is allowed to stand overnight at room temperature and is evaporated again, and the residue is chromatographed over silica gel using ethylene chloride. The fractions having an Rf-value of 0.6 are combined and evaporated. This gives a colourless oil.

Yield: 2.4 g (72% of theory)

NMR spectrum (in CDCl$_3$-CD$_3$OD): CH and 7 aliphatic H has multiplets at 4.0 and at 2.4–3.4 ppm, CH$_3$=doublet at 1.15 ppm.

EXAMPLE 35

3-(2-Benzenesulphonamido-indan-5-yl)-butyric acid 2.4 g of methyl 3-(2-benzenesulphonamido-indan-5-yl)-butyrate are dissolved in 10 ml of ethanol, 2 ml of 15N sodium hydroxide solution are added, and saponification is carried out by boiling for 1 hour.

The mixture is evaporated, the residue is dissolved in water, and the free acid is precipitated as a foamy material by adding hydrochloric acid.

Yield: 2.0 g (87% of theory)

Melting point: 40° C.

C$_{19}$H$_{21}$NO$_4$S (359.45) Calculated: C 63.49 H 5.89 N 3.90 S 8.92 Found: 63.88 6.01 3.83 8.66

EXAMPLE 36

Methyl 3-(2-benzenesulphonamido-indan-5-yl)-butyrate 3 ml of perchloric acid and 1 g of 10% palladium-on-charcoal are added to 4.7 g (12.5 mmol) of 4-(2-benzenesulphonamido-indan-5-yl)-oxobutyric acid in 60 ml of glacial acetic acid, and the mixture is hydrogenated at 50° C. under a hydrogen pressure of 5 bar. The mixture is evaporated, water is added to the residue, and the reaction product is extracted with ethyl acetate. After evaporation of the extract, the residue is dissolved in 20 ml of methanol, and 2 ml of thionyl chloride are added at −50° C. After the mixture has stood overnight, it is again evaporated and the residue is chromatographed over silica gel using 98:2 ethylene chloride/methanol. The fractions having an Rf-value of 0.7 (silica gel-polygram plates; 95:5 chloroform/methanol) are combined and evaporated.

Yield: 1.4 g (30% of theory).

EXAMPLE 37

4-(2-Benzenesulphonamido-indan-5-yl)-butyric acid

Prepared analogously to Example 35 from methyl 4-(2-benzenesulphonamido-indan-5-yl)-butyrate by hydrolysis with sodium hydroxide.

Yield: 81% of theory,

Oil, Rf-value: 0.5 (silica gel-polygram plates; mobile phase: 1:1 cyclohexane/ethyl acetate)

NMR spectrum (in CDCl$_3$-CD$_3$OD) CH and 10 aliphatic H: multiplets at 4.1 and 1.8–3.3 ppm.

EXAMPLE 38

Methyl 4-(2-p-chlorobenzenesulphonamido-indan-5-yl)butyrate 1.6 g (16 mmol) of triethylamine, followed by 3.2 g (14.4 mmol) of p-chlorobenzenesulphonyl chloride are added to 2.8 g (12 mmol) of methyl 4-(2-amino-indan-5-yl)-butyrate in 40 ml of chloroform. The mixture is stirred for 3 hours at room temperature, water is added, the chloroform phase is evaporated, and the reaction product is purified by chromatography over silica gel using chloroform.

Yield: 4.0 g (81.7% of theory)

Oil, Rf-value: 0.7 (Merck silica gel-polygram plates; mobile phase: 1:1 cyclohexane/ethyl acetate).

IR spectrum (in methylene chloride): NH at 3360 cm$^{-1}$, OCH$_3$ at 2840 cm$^{-1}$, ester-CO at 1735 cm$^{-1}$, SO$_2$ at 1160+1340 cm$^{-1}$.

Melting point: 82°–85° C. (methanol)

C$_{20}$H$_{22}$ClNO$_4$S (407.91) Calculated: C 58.89 H 5.43 N 3.43 Cl 8.69 S 7.86 Found: 58.67 5.18 3.35 8.76 7.98

EXAMPLE 39

4-(2-p-Chlorobenzenesulphonamido-indan-5-yl)-butyric acid

Prepared analogously to Example 35 from methyl 4-(2-p-chlorobenzenesulphonamido-indan-5-yl)-butyrate by hydrolysis with sodium hydroxide.

Yield: 72% of theory,

Melting point: 131°–133° C. (ethyl acetate/diisopropyl ether)

C$_{19}$H$_{20}$ClNO$_4$S (393.88) Calculated: C 57.94 H 5.12 N 3.56 Cl 9.00 S 8.14 Found: 57.65 5.33 3.59 9.06 8.22

EXAMPLE 40

Methyl 4-(2-p-toluenesulphonamido-indan-5-yl)-butyrate

Prepared analogously to Example 1 from methyl 4-(2-amino-indan-5-yl)-butyrate by means of p-toluenesulphonyl chloride.

Yield: 69% of theory,

Melting point: 97°–99° C. (diisopropyl ether)

C$_{21}$H$_{25}$NO$_4$S (387.49) Calculated: C 65.09 H 6.50 N 3.61 S 8.27 Found: 64.90 6.65 3.51 8.18

EXAMPLE 41

4-(2-p-Toluenesulphonamido-indan-5-yl)-butyric acid

Prepared analogously to Example 35 from methyl 4-(2-p-toluenesulphonamido-indan-5-yl)-butyrate by hydrolysis with sodium hydroxide.

Yield: 67% of theory,

Melting point: 130°–132° C. (acetic acid/diisopropyl ether)

C$_{20}$H$_{23}$NO$_4$S (373.47) Calculated: C 64.32 H 6.21 N 3.75 S 8.58 Found: 64.40 6.41 3.65 8.53

EXAMPLE 42

Methyl 4-(2-o-toluenesulphonamido-indan-5-yl)-butyrate

Prepared analogously to Example 1 from methyl 4-(2-amino-indan-5-yl)-butyrate and o-toluenesulphonyl chloride.

Yield: 82% of theory,

Oil, Rf-value: 0.7 (on Merck silica gel-polygram plates; mobile phase: 1:1 cyclohexane/ethyl acetate).

IR spectrum (in methylene chloride): NH at 3370 cm$^{-1}$, ester-CO at 1735 cm$^{-1}$, SO$_2$ at 1160 and 1335 cm$^{-1}$.

EXAMPLE 43

4-(2-o-Toluenesulphonamido-indan-5-yl)-butyrate

Prepared analogously to Example 35 from methyl 4-(2-o-toluenesulphonamido-indan-5-yl)-butyrate by hydrolysis with sodium hydroxide.

Yield: 90% of theory,

Oil, Rf-value: 0.5 (on Merck silica gel-polygram plates; mobile phase: 1:1 cyclohexane/ethyl acetate).

C$_{20}$H$_{23}$NO$_4$S (373.47) Calculated: N 3.75 S 8.58 Found: 3.31 8.45

EXAMPLE 44

4-Hydroxy-4-(2-p-toluenesulphonamido-indan-5-yl)-butyric acid 400 mg (1.03 mmol) of 4-(2-p-toluenesulphonamido-indan-5-yl)-oxobutyric acid are dissolved in 2 ml of 2N sodium hydroxide solution and are diluted with 10 ml of water, and 20 mg of sodium borohydride are added. The mixture is allowed to stand overnight and is acidified, and the reaction product is extracted with ethyl acetate. The residue from evaporation is triturated with petroleum ether. This gives 400 mg (100% of theory) of a crystalline material which sinters above 60° C.

Rf-value: 0.3 (Merck silica gel-polygram plates; mobile phase, 90:10:10:6 toluene/dioxan/ethanol/glacial acetic acid).

IR spectrum (in methylene chloride): OH at 3600 cm$^{-1}$, NH at 3360 cm$^{-1}$, CO at 1780, 1750 and 1710 cm$^{-1}$, SO$_2$ at 1160 and 1340 cm$^{-1}$.

EXAMPLE 45

Methyl (2-p-chlorobenzenesulphonamido-indan-5-yl)-acetate

Prepared analogously to Example 5 from methyl (2-amino-indan-5-yl)-acetate hydrochloride and p-chlorobenzenesulphonyl chloride in chloroform in the presence of triethylamine. Purified by column chromatography over silica gel using 98:2 ethylene chloride/methanol.

Yield: 20% of theory,

Oil, Rf-value: 0.8 (silica gel-polygram plates; mobile phase: 95:5 chloroform/methanol).

IR spectrum (in methylene chloride): NH at 3360 cm$^{-1}$, CO at 1740 cm$^{-1}$, SO$_2$ at 1160 and 1340 cm$^{-1}$.

EXAMPLE 46

(2-p-Chlorobenzenesulphonamido-indan-5-yl)-acetic acid

Prepared analogously to Example 2 from methyl (2-p-chlorobenzenesulphonamido-indan-5-yl)-acetate by hydrolysis with sodium hydroxide.

Yield: 67% of theory,

Melting point: 156°–158° C. (from toluene)

C$_{17}$H$_{16}$ClNO$_4$S (365.83) Calculated: C 55.81 H 4.41 N 3.83 Cl 9.69 S 8.76 Found: 56.47 4.45 4.00 9.94 8.98

EXAMPLE 47

Methyl (2-p-toluenesulphonamido-indan-5-yl)-acetate

Prepared analogously to Example 5 from methyl (2-amino-indan-5-yl)-acetate hydrochloride and p-toluenesulphochloride in chloroform in the presence of triethylamine. Purified by column chromatography over silica gel using 98:2 ethylene chloride/methanol.

Yield: 63% of theory,

Oil, Rf-value: 0.8 (silica gel-polygram plates; mobile phase: 95:5 chloroform/methanol).

IR spectrum (in methylene chloride): NH at 3360 cm$^{-1}$, OCH$_3$ at 2840 cm$^{-1}$, CO at 1735 cm$^{-1}$, SO$_2$ at 1160 and 1340 cm$^{-1}$.

EXAMPLE 48

(2-p-Toluenesulphonamido-indan-5-yl)-acetic acid

Prepared analogously to Example 2 from methyl (2-p-toluenesulphonamido-indan-5-yl)-acetate by hydrolysis with sodium hydroxide.

Yield: 71% of theory,

Melting point: 143°–145° C. (from toluene)

C$_{18}$H$_{19}$NO$_4$S (345.41) Calculated: C 62.59 H 5.54 N 4.06 S 9.28 Found: 62.82 5.41 4.03 9.39

EXAMPLE 49

Methyl (2-o-toluenesulphonamido-indan-5-yl)-acetate

Prepared analogously to Example 5 from methyl (2-amino-indan-5-yl)-acetate hydrochloride and o-toluenesulphonyl chloride in chloroform in the presence of triethylamine. Purified by column chromatography over silica gel using 98:2 ethylene chloride/methanol.

Yield: 10% of theory,

Oil, Rf-value: 0.85 (silica gel-polygram plates; mobile phase: 95:5 chloroform/methanol).

IR spectrum (in methylene chloride): NH at 3370 cm$^{-1}$, OCH$_3$ at 2840 cm$^{-1}$, CO at 1740 cm$^{-1}$, SO$_2$ at 1160 and 1335 cm$^{-1}$.

EXAMPLE 50

(2-o-Toluenesulphonamido-indan-5-yl)-acetic acid

Prepared analogously to Example 2 from methyl (2-o-toluenesulphonamido-indan-5-yl)-acetate by hydrolysis with sodium hydroxide.

Yield: 30% of theory,

Resin, Rf-value: 0.5 (silica gel plates F 254 made by Merck, Darmstadt; mobile phase: 90:10:10:6 toluene/dioxan/ethanol/glacial acetic acid).

C$_{18}$H$_{19}$NO$_4$S (345.41) Calculated: C 62.59 H 5.54 N 4.06 S 9.28 Found: 62.80 5.62 4.19 9.05

EXAMPLE 51

Methyl (2-p-methoxybenzenesulphonamido-indan-5-yl)-acetate

Prepared analogously to Example 5 from methyl (2-amino-indan-5-yl)-acetate hydrochloride and p-methoxybenzenesulphonyl chloride in chloroform in the presence of triethylamine. Purified by column chromatography over silica gel using 98:2 ethylene chloride/methanol.

Yield: 56% of theory,

Oil, Rf-value: 0.7 (silica gel-polygram plates; mobile phase: 95:5 chloroform/methanol).

IR spectrum (in methylene chloride): NH at 3360 cm$^{-1}$, OCH$_3$ at 2840 cm$^{-1}$, SO$_2$ at 1150 and 1340 cm$^{-1}$.

EXAMPLE 52

(2-p-Methoxybenzenesulphonamido-indan-5-yl)-acetic acid

Prepared analogously to Example 2 from methyl (2-p-methoxybenzenesulphonamido-indan-5-yl)-acetate by hydrolysis with sodium hydroxide.

Yield: 73% of theory,

Melting point: 156°–158° C. (from ethyl acetate/diisopropyl ether).

$C_{18}H_{19}NO_5S$ (361.41) Calculated: C 59.82 H 5.30 N 3.88 S 8.87 Found: 60.13 5.24 3.88 8.75

EXAMPLE 53

Methyl (2-o-methoxybenzenesulphonamido-indan-5-yl)-acetate

Prepared analogously to Example 5 from methyl (2-amino-indan-5-yl)-acetate hydrochloride and o-methoxybenzenesulphonylbromide in chloroform in the presence of triethylamine. Purified by column chromatography over silica gel using 99:1 ethylene chloride/methanol as mobile phase.

Yield: 75% of theory,

Oil, Rf-value: 0.7 (silica gel-polygram plates; mobile phase: 95:5 chloroform/methanol).

IR spectrum (in methylene chloride): NH at 3350 $cm^{-1}$, $OCH_3$ at 2840 $cm^{-1}$, $SO_2$ at 1160 and 1340 $cm^{-1}$.

EXAMPLE 54

(2-o-Methoxybenzenesulphonamido-indan-5-yl)-acetic acid

Prepared analogously to Example 2 from methyl (2-o-methoxybenzenesulphonamido-indan-5-yl)-acetate by hydrolysis with sodium hydroxide.

Yield: 60% of theory,

Melting point: 134°–136° C. (from ethyl acetate/diisopropyl ether).

$C_{18}H_{19}NO_5S$ (361.41) Calculated: C 59.82 H 5.30 N 3.88 S 8.87 Found: 59.80 5.37 3.79 8.73

EXAMPLE 55

Methyl [2-(2,5-dichlorobenzenesulphonyl)-amido-indan-5-yl]-acetate

Prepared analogously to Example 5 from methyl (2-amino-indan-5-yl)-acetate hydrochloride and 2,5-dichlorobenzenesulphonyl chloride in chloroform in the presence of triethylamine. Purified by column chromatography over silica gel using 99:1 ethylene chloride/methanol as mobile phase.

Yield: 64% of theory,

Oil, Rf-value: 0.8 (silica gel-polygram plates; mobile phase: 95:5 chloroform/methanol).

IR spectrum (in methylene chloride): NH at 3360 $cm^{-1}$, CO at 1740 $cm^{-1}$, $SO_2$ at 1165 and 1350 $cm^{-1}$.

EXAMPLE 56

[2-(2,5-Dichlorobenzenesulphonyl)-amido-indan-5-yl]acetic acid

Prepared analogously to Example 2 from methyl [2-(2,5-dichlorobenzenesulphonyl)amido-indan-5-yl]acetate by hydrolysis with sodium hydroxide.

Yield: 57% of theory,

Melting point: 172°–174° C. (from ethyl acetate/diisopropyl ether/petroleum ether).

$C_{17}H_{15}Cl_2NO_4S$ (400.28) Calculated: C 51.01 H 3.78 Cl 17.71 N 3.50 S 8.01 Found: 51.03 3.87 17.81 3.52 8.03

EXAMPLE 57

Methyl (2-p-fluorobenzenesulphonamido-indan-5-yl)-acetate

Prepared analogously to Example 5 from methyl (2-amino-indan-5-yl)-acetate hydrochloride and p-fluorobenzenesulphonyl chloride in chloroform in the presence of triethylamine. Purified by column chromatography over silica gel using 98:2 ethylene chloride/methanol as mobile phase.

Yield: 54% of theory,

Oil, Rf-value: 0.8 (silica gel-polygram plates; mobile phase: 95:5 chloroform/methanol).

IR spectrum (in methylene chloride): NH at 3360 $cm^{-1}$, CO at 1735 $cm^{-1}$, $SO_2$ at 1150 and 1340 $cm^{-1}$.

EXAMPLE 58

(2-p-Fluorobenzenesulphonamido-indan-5-yl)-acetic acid

Prepared analogously to Example 2 from methyl (2-p-fluorobenzenesulphonamido-indan-5-yl)-acetate by hydrolysis with sodium hydroxide.

Yield: 43% of theory,

Melting point: 129.5°–131.5° C. (from ethyl acetate/diisopropyl ether).

$C_{17}H_{16}FNO_4S$ (349.38) Calculated: C 58.44 H 4.61 N 4.01 S 9.18 Found: 58.60 4.63 3.95 9.37

EXAMPLE 59

2-(2-p-Toluenesulphonamido-indan-5-yl)-propionate 3.2 g (0.0125 mol) of methyl 2-(2-amino-indan-5-yl)propionate hydrochloride and 2.7 g (0.014 mol) of p-toluenesulphonyl chloride are dissolved in chloroform, and 2.53 g (0.025 mol) of triethylamine are added dropwise, with stirring. The mixture is allowed to stand overnight at room temperature. Water is then added and the chloroform phase is separated off and evaporated in vacuo. The residue from this (4.6 g) is chromatographed over 300 g of silica gel using 98:2 ethylene chloride/ethanol.

Yield: 1.2 g (26% of theory),

Oil, Rf-value=0.2 (on silica gel-polygram plates SIL G/UV made by Macherey-Nagel, Duren; mobile phase: ethylene chloride.

EXAMPLE 60

2-(2-p-Toluenesulphonamido-indan-5-yl)-propionic acid 1 ml of 15N sodium hydroxide solution is added to 1.2 g of methyl 2-(2-p-toluenesulphonamido-indan-5-yl)-propionate in 12 ml of ethanol and the mixture is boiled for 0.5 hour. The mixture is evaporated, the residue is dissolved in water and the reaction product is precipitated with hydrochloric acid.

Yield: 1.0 g (87% of theory), of an oil which solidifies slowly.

$C_{19}H_{21}NO_4S$ (359.44) Calculated: C 63.49 H 5.89 N 3.90 S 8.92 Found: 63.38 6.19 3.92 9.22

IR spectrum (in methylene chloride): NH at 3360 $cm^{-1}$, CO at 1715 and 1750 $cm^{-1}$, $SO_2$ at 1160 and 1340 $cm^{-1}$.

EXAMPLE 61

Methyl 2-(2-p-chlorobenzenesulphonamido-indan-5-yl)-propionate

Prepared analogously to Example 59 from methyl 2-(2-amino-indan-5-yl)-propionate hydrochloride and p-chlorobenzenesulphonyl chloride in chloroform in the presence of triethylamine.

Yield: 15% of theory,

Oil, Rf-value=0.2 (on silica gel-polygram plates SIL G/UV made by Macherey-Nagel, Duren; mobile phase: ethylene chloride).

EXAMPLE 62

2-(2-p-Chlorobenzenesulphonamido-indan-5-yl)-propionic acid

Prepared analogously to Example 6 from methyl 2-(2-p-chlorobenzenesulphonamido-indan-5-yl)propionate by hydrolysis with sodium hydroxide.

Yield: 69% of theory,

Melting point: 87°–90° C.

$C_{18}H_{18}ClNO_4S$ (379.86) Calculated: C 56.92 H 4.78 N 3.69 Cl 9.33 S 8.44 Found: 56.95 4.71 3.64 9.41 8.27

EXAMPLE 63

Ethyl 2-carbethoxy-4-(2-p-toluenesulphonamido-indan-5-yl)-4-oxobutyrate 10.6 g (0.095 mol) of potassium tert.-butanolate, followed by 23.0 g (0.063 mol) of (2-p-toluenesulphonamido-indan-5-yl) chloromethyl ketone, are added to 15.2 g (0.095 mol) of diethyl malonate in 25 ml of dimethyl sulphoxide. The mixture is allowed to stand overnight and is neutralised with glacial acetic acid, and water and petroleum ether are added. The reaction product which is precipitated is separated off and dissolved in ethyl acetate. The organic phase is washed with water, dried and evaporated, and the residue obtained is purified by chromatography over 600 g of silica gel using 98:2 ethylene chloride/ethanol.

Yield: 20.2 g (65.5% of theory),

Melting point: 101°–103° C. (ethyl acetate/petroleum ether)

$C_{25}H_{29}NO_7S$ (487.57) Calculated: C 61.59 H 5.99 N 2.87 S 6.58 Found: 61.29 6.00 2.98 6.42

The following is prepared analogously:

Ethyl 2-carbethoxy-4-(2-p-chlorobenzenesulphonamido-indan-5-yl)-4-oxobutyrate

Yield: 96% of theory,

Oil, Rf-value: 0.4 (silica gel-polygram plates SIL G/UV made by Macherey-Nagel, Duren; mobile phase: 3:1 cyclohexane/ethyl acetate).

EXAMPLE 64

4-Carbethoxy-6-(2-p-chlorobenzenesulphonamido-indan-5-yl)-4,5-dihydropyridazin-3(2H)-one Prepared analogously to Example 26 from ethyl 2-carbethoxy-4-(2-p-chlorobenzenesulphonamido-indan-5-yl)-4-oxobutyrate and hydrazine, by boiling in glacial acetic acid.

Yield: 38% of theory,

Melting point: 174°–177° C. (glacial acetic acid)

$C_{22}H_{22}ClN_3O_5S$ (475.95) Calculated: C 55.52 H 4.66 N 8.33 Cl 7.45 S 6.74 Found: 55.53 4.59 8.50 7.36 6.64

IR spectrum (in KBr): ester-CO 1725 cm$^{-1}$, SO$_2$NH at 1160 and 1340 cm$^{-1}$.

EXAMPLE 65

4-Carbethoxy-6-(2-p-toluenesulphonamido-indan-5-yl)-4,5-di-hydropyridazin-3(2H)-one Prepared analogously to Example 26 from ethyl 2-carbethoxy-4-(2-p-toluenesulphonamido-indan-5-yl)-4-oxobutyrate and hydrazine, by boiling in glacial acetic acid.

Yield: 82% of theory,

Melting point: 187°–189° C. (glacial acetic acid)

$C_{23}H_{25}N_3O_5S$ (455.53) Calculated: C 60.64 H 5.53 N 9.22 S 7.04 Found: 60.25 5.55 9.66 7.10

IR spectrum (in KBr): Ester-CO 1740 cm$^{-1}$, lactam-CO at 1665 cm$^{-1}$, C=N at 1615 cm$^{-1}$, SO$_2$NH at 1150 and 1330 cm$^{-1}$.

EXAMPLE 66

6-(2-p-Toluenesulphonamido-indan-5-yl)-4,5-dihydro-pyridazin-3(2H)-one 600 mg (15 mmol) of sodium hydroxide in 2 ml of water are added to 2.3 g (5 mmol) of 4-carbethoxy-6-(2-p-toluolesulfonamido-indan-5-yl)-dihydro-pyridazin-3(2H)-one in 40 ml of ethanol, and the mixture is stirred over night in order to achieve hydrolysis. The reaction product which is precipitated on acidifying is filtered off with suction and heated in glacial acetic acid for 10 minutes at the boil. The desired compound crystallises out on cooling.

Yield: 1.8 g (93% of theory),

Melting point: 185°–187° C.

EXAMPLE 67

6-(2-p-Chlorobenzenesulfonamido-indan-5-yl)-4,5-dihydropyridazin-3(2H)-one

Prepared analogously to Example 66 from 4-carbethoxy-6-(2-p-chlorobenzenesulfonamido-indan-5-yl)-4,5-dihydro-pyridazin-3(2H)-one by hydrolysis and decarboxylation.

Yield: 67% of theory,

Melting point: 203°–205° C.

EXAMPLE I

Tablets containing 100 ml of 4-(2-p-toluenesulfonamido-indan-5-yl)-4-oxobutyric acid

| Composition | |
|---|---|
| 1 Tablet contains: | |
| Active compound | 100.0 mg |
| Lactose | 80.0 mg |
| Maize starch | 34.0 mg |
| Polyvinylpyrrolidone | 4.0 mg |
| Magnesium stearate | 2.0 mg |
| | 220.0 mg |

Process of preparation:

The active compound, the lactose and the starch are mixed and moistened uniformly with an aqueous solution of the polyvinylpyrrolidone. The moist composition is screened (2.0 mm mesh size) and dried at 50° C. in a tray drying cabinet and is then again screened (1.5 mm mesh size), and the lubricant is mixed in. The mixture is compressed into tablets.

Tablet weight: 220 mg
Diameter 9 mm, biplanar, beveled on both sides and with a dividing groove on one side.

EXAMPLE II

Hard gelatine casules containing 150 mg of 4-(2-p-toluenesulfonamido-indan-5-yl)-4-oxobutyric acid

| 1 Capsule contains: | | |
|---|---|---|
| Active compound | | 150.0 mg |
| Maize starch, dried | approx. | 180.0 mg |
| Lactose, powdered | approx. | 87.0 mg |
| Magnesium stearate | | 3.0 mg |
| | approx. | 320.0 mg |

Preparation:

The active compound is mixed with the auxiliaries, put through a sieve of mesh size 0.75 mm and made into a homogeneous mixture in a suitable device. The final mixture is filled into hard gelatine capsules of size 1.
Capsule filling: approx. 320 mg.
Capsule shell: hard gelatine capsules, size 1.

EXAMPLE III

Suppositories containing 150 mg of 4-(2-p-toluene-sulfonamido-indan-5-yl)-4-oxobutyric acid

| 1 Suppository containings: | |
|---|---|
| Active compound | 150.0 mg |
| Polyethylene glycol (MW 1500) | 550.0 mg |
| Polyethylene glycol (MW 6000) | 460.0 mg |
| Polyethylene sorbitan monostearate | 840.0 mg |
| | 2,000.0 mg |

Preparation:

The suppository constituents are melted and the active compound is distributed therein homogeneously and the melt is poured into pre-cooled moulds.

EXAMPLE IV

Suspensions containing 50 mg of 4-(2-p-toluene-sulfonamido-indan-5-yl)-4-oxobutyric acid

| 100 ml of the suspension contains: | | |
|---|---|---|
| Active compound | | 1.0 g |
| Na salt of carboxymethylcellulose | | 0.2 g |
| Methyl p-hydroxybenzoate | | 0.05 g |
| Propyl p-hydroxybenzoate | | 0.01 g |
| Glycerol | | 5.0 g |
| Sorbitol solution, 70% strength | | 50.0 g |
| Aroma | | 0.3 g |
| Distilled water | ad. | 100 ml |

Preparation:

The distilled water is heated to 70° C. The methyl and propyl p-hydroxybenzoates and the glycerol and sodium salt of carboxymethylcellulose are dissolved in the distilled water. The solution is cooled to room temperature, and the active compound is added with stirring and dispersed homogeneously. After the sorbitol solution and the aroma have been added, the suspension is evacuated, with stirring, to remove air from it.
5 ml of the suspension contain 50 mg of active compound.

EXAMPLE V

Tablets containing 150 mg of (2-p-chlorobenzene-sulfonamido-indan-5-yl)-acetic acid

| Composition 1 tablet contains: | |
|---|---|
| Active substance | 150.0 mg |
| Lactose, powdered | 89.0 mg |
| Maize starch | 40.0 mg |
| Colloidal silica | 10.0 mg |
| Polyvinylpyrrolidone | 10.0 mg |
| Magnesium stearate | 1.0 mg |
| | 300.0 mg |

Preparation:

The active substance is mixed with the lactose, maize, starch and silica and is moistened with a 20% aqueous solution of the polyvinylpyrrolidone and forced through a sieve of mesh size 1.5 mm.
The granules are dried at 45° C. and are rubbed through the same sieve again and mixed with the amount of magnesium stearate indicated. The mixture is compressed into tablets.
Table weight: 300 mg
Die: 10 mm, flat.

EXAMPLE VI

Film tablets containing 75 mg of (2-p-chlorobenzene-sulfonamido-indan-5-yl)-acetic acid

| 1 Tablet core contains: | |
|---|---|
| Active substance | 75.0 mg |
| Calcium phosphate | 93.0 mg |
| Maize starch | 35.5 mg |
| Polyvinylpyrrolidone | 10.0 mg |
| Hydroxypropylmethylcellulose | 15.0 mg |
| Magnesium stearate | 1.5 mg |
| | 230.0 mg |

Preparation:

The active substance is mixed with the calcium phosphate, maize starch, polyvinylpyrrolidone, hydroxypropylmethylcellulose and half the indicated amount of magnesium stearate. Mouldings having a diameter of 13 mm are prepared on a tableting machine and are rubbed, on a suitable machine, through a sieve of mesh size 1.5 mm and mixed with the remaining amount of magnesium stearate. These granules are pressed on a tableting machine to give tablets of the desired shape.
Core weight: 230 mg
Die: 9 mm, domed
The tablet cores thus prepared are coated with a film consisting essentially of hydroxypropylmethylcellulose. The finished film tablets are glazed with beeswax.
Film tablet weight: 245 mg
All the other compounds of the general formula I can, of course, be used as active compounds in the above pharmaceutical formulations.

What is claimed is:

1. Benzenesulphonamidoindanyl compounds of the general formula

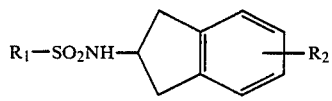 (I)

in which
R$_1$ is phenyl optionally mono- or di- substituted by halo, methyl or methoxy, and
R$_2$ is hydroxycarbonyl or (C$_1$–C$_3$-alkoxy)carbonyl, which groups are optionally attached via C$_1$–C$_5$ alkylene or C$_2$–C$_5$ alkenylene in which optional attachment the methylene group attached to the indanyl may be replaced by hydroxymethylene or carbonyl and further for the methylene group via which the C$_2$–C$_4$ alkoxycarbonyl is attached to be substituted by a further C$_2$–C$_4$ alkoxycarbonyl.

2. The compounds as recited in claim 1 wherein R$_1$ is phenyl optionally substituted by methyl or methoxy or a phenyl optionally mono- or disubstituted by fluoro, chloro or bromo and wherein R$_2$ is hydroxycarbonyl or (C$_1$–C$_2$-alkoxy)carbonyl, which groups are optionally attached via C$_1$–C$_4$ alkylene or C$_2$–C$_4$ alkenylene, in which optional attachment the methylene group attached to the indanyl may be replaced by hydroxymethylene or carbonyl.

3. The compounds as recited in claim 2 wherein R$_1$ is phenyl optionally substituted by fluoro, chloro, methyl or methoxy and wherein R$_2$ is hydroxycarbonylmethyl, 4-hydroxy-carbonyl-n-propyl or 3-hydroxycarbonyl-n-propanon-1-yl.

4. The compounds as recited in claim 1 wherein R$_2$ is hydroxycarbonylmethyl, 4-hydroxycarbonyl-n-propyl or 3-hydroxycarbonyl-n-propanon-1-yl.

5. 4-(2-p-Toluenesulfonamido-indan-5-yl)-4-oxobutyric acid and addition salts thereof with inorganic bases.

6. (2-p-Chlorobenzenesulfonamido-indan-5-yl)-acetic acid and addition salts thereof with inorganic bases.

7. 4-(2-p-Chlorobenzenesulfonamido-indan-5-yl)-butyric acid and acid addition salts thereof with inorganic bases.

* * * * *

UNITED STATES PATENT AND TRADEMARK OFFICE
CERTIFICATE OF CORRECTION

PATENT NO. : 4,929,754
DATED : May 29, 1990
INVENTOR(S) : Josef Nickl et al.

It is certified that error appears in the above-identified patent and that said Letters Patent is hereby corrected as shown below:

Column 3, lines 52 through 53 shall read:

"$R_2$ denotes a hydroxycarbonylmethyl, 3-hydroxycarbonyl-n-propyl, 3-hydroxycarbonyl-n-propanon-1-yl,..."

Claim 3 shall read:

3. The compounds as recited in Claim 2 wherein $R_1$ is phenyl optionally substituted by fluoro, chloro, methyl or methoxy and wherein $R_2$ is hydroxycarbonylmethyl, 3-hydroxycarbonyl-n-propyl or 3-hydroxycarbonyl-n-propanon-1-yl.

Claim 4 shall read:

4. The compounds as recited in Claim 1 wherein $R_2$ is hydroxycarbonylmethyl, 3-hydroxycarbonyl-n-propyl or 3-hydroxycarbonyl-n-propanon-1-yl.

Signed and Sealed this

Sixth Day of October, 1992

Attest:

DOUGLAS B. COMER

Attesting Officer    Acting Commissioner of Patents and Trademarks